(12) United States Patent
Egawa

(10) Patent No.: US 7,935,854 B2
(45) Date of Patent: May 3, 2011

(54) STILBENE DERIVATIVE, LIGHT-EMITTING ELEMENT, DISPLAY APPARATUS, AND ELECTRONIC APPLIANCE

(75) Inventor: Masakazu Egawa, Tochigi (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 725 days.

(21) Appl. No.: 11/865,333

(22) Filed: Oct. 1, 2007

(65) Prior Publication Data
US 2008/0081934 A1    Apr. 3, 2008

(30) Foreign Application Priority Data
Oct. 3, 2006   (JP) .................................. 2006-271698

(51) Int. Cl.
*C07C 15/20* (2006.01)
*C07C 15/27* (2006.01)
(52) U.S. Cl. .......................................... 585/26; 585/25
(58) Field of Classification Search .................... 585/24, 585/25, 26
See application file for complete search history.

(56) References Cited

U.S. PATENT DOCUMENTS

| | | | |
|---|---|---|---|
| 5,073,465 A | 12/1991 | Makino et al. | |
| 5,085,946 A | 2/1992 | Saito et al. | |
| 6,046,348 A | 4/2000 | Yamada et al. | |
| 6,066,712 A | 5/2000 | Ueda et al. | |
| 6,468,675 B1 | 10/2002 | Ishikawa et al. | |
| 6,653,034 B2 | 11/2003 | Inagaki et al. | |
| 6,743,948 B1 | 6/2004 | Hosokawa et al. | |
| 6,951,693 B2 | 10/2005 | Hosokawa et al. | |
| 7,053,255 B2 | 5/2006 | Ikeda et al. | |
| 7,402,346 B2 * | 7/2008 | Coggan et al. ................. | 428/690 |
| 7,476,745 B2 * | 1/2009 | Egawa et al. ................. | 548/440 |
| 7,612,204 B2 * | 11/2009 | Egawa et al. ................. | 544/353 |
| 7,638,663 B2 * | 12/2009 | Egawa et al. .................. | 585/26 |

(Continued)

FOREIGN PATENT DOCUMENTS
EP      1 333 018 A1     8/2003
(Continued)

OTHER PUBLICATIONS

Cha, S.W. et al, "Electroluminescence of LEDs Consisting Two Layers of Alq$_3$ and High T$_g$, Blue-Light Emitting Branched Compounds," Synthetic Metals, vol. 143, No. 1, 2004, pp. 97-101.

*Primary Examiner* — Ellen M McAvoy
(74) *Attorney, Agent, or Firm* — Husch Blackwell LLP

(57) ABSTRACT

An object of the present invention is to provide a novel material having heat resistance which provides blue light emission, and a light-emitting element, a display apparatus, and an electronic appliance using the material. Aspects of the invention are a stilbene derivative represented by the following general formula (1), the light-emitting element in which a layer containing a light-emitting material interposed between two electrodes is included and the stilbene derivative is contained in the layer containing a light-emitting material, the display apparatus including the light-emitting element, and the electronic appliance including the display apparatus.

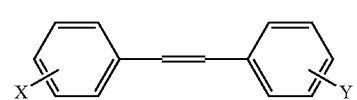

(1)

5 Claims, 13 Drawing Sheets

U.S. PATENT DOCUMENTS

| | | | |
|---|---|---|---|
| 7,674,914 B2 * | 3/2010 | Egawa et al. | 548/427 |
| 7,732,619 B2 * | 6/2010 | Egawa et al. | 548/427 |
| 7,758,972 B2 * | 7/2010 | Egawa et al. | 428/690 |
| 2003/0072966 A1 | 4/2003 | Hosokawa et al. | |
| 2003/0222575 A1 | 12/2003 | Yamazaki et al. | |
| 2006/0083947 A1 | 4/2006 | Ikeda et al. | |
| 2006/0189828 A1 | 8/2006 | Hosokawa et al. | |
| 2007/0080630 A1 | 4/2007 | Egawa et al. | |
| 2007/0100180 A1 * | 5/2007 | Egawa et al. | 585/26 |
| 2007/0142671 A1 | 6/2007 | Hosokawa et al. | |
| 2007/0215889 A1 | 9/2007 | Kawakami et al. | |
| 2008/0088229 A1 * | 4/2008 | Egawa | 313/504 |
| 2008/0091030 A1 | 4/2008 | Egawa et al. | |
| 2009/0146558 A1 | 6/2009 | Egawa et al. | |

FOREIGN PATENT DOCUMENTS

| | | |
|---|---|---|
| JP | 2-291696 | 12/1990 |
| JP | 4-361269 | 12/1992 |
| JP | 2001-335516 | 12/2001 |
| JP | 2004-75580 | 3/2004 |
| JP | 2004-196716 | 7/2004 |
| WO | WO 00/39247 A1 | 7/2000 |

* cited by examiner

STILBENE DERIVATIVE, LIGHT-EMITTING ELEMENT, DISPLAY APPARATUS, AND ELECTRONIC APPLIANCE

BACKGROUND OF THE INVENTION

1. Field of the Invention

The present invention relates to a light-emitting material, a light-emitting element containing the light-emitting material, and a display apparatus and an electronic appliance including such a light-emitting element.

2. Description of the Related Art

A light-emitting element containing a light-emitting material is characterized by thinness, lightness in weight, fast response, direct-current low-voltage driving, and so on. The light-emitting element is expected to be applied to a flat panel display of the next generation. Further, a light-emitting device with the light-emitting elements disposed in matrix has a wide viewing angle compared to a conventional liquid crystal display device, so that the light-emitting device is excellent in visibility.

Light emission mechanism of the light-emitting element will be described. When voltage is applied to a light-emitting layer interposed between a pair of electrodes, electrons injected from a cathode and holes injected from an anode are recombined in the light emission center of the light-emitting layer, and molecular excitons are formed. Then, the molecular excitons release light energy in returning to a ground state; consequently, light emission is generated.

A light emission wavelength of the light-emitting element is determined depending on the band gap of a light-emitting molecule contained in the light-emitting element. Thus, light-emitting elements having various kinds of light emission colors can be obtained by devising a structure of the light-emitting molecule. Further, a full color light-emitting device can be manufactured with the use of a red light-emitting element, a blue light-emitting element, and a green light-emitting element.

A red light-emitting element, a green light-emitting element, and a blue light-emitting element are necessary in order to manufacture a full color light-emitting device. However, the development for a highly reliable blue light-emitting material lags behind that of the red light-emitting material or the green light-emitting material. Many studies have been made about the blue light-emitting element in order to solve this problem. (for example, see Patent Document 1: Japanese Published Patent Application No. 2001-335516).

SUMMARY OF THE INVENTION

Patent Document 1 discloses some compounds formed by combination of an anthracene skeleton and a stilbene skeleton. However, as described in Embodiment of Patent Document 1, the glass transition point Tg is less than or equal to 135° C. (with reference to (25), (26), (33), and (34) of Table 2 in paragraph [0086] of Patent Document 1, Tg (glass transition point) is 130° C., 135° C., 105° C., 110° C., respectively.). The development for a material having higher heat resistance is necessary in order to obtain a more reliable blue light-emitting material.

The present invention has been made in view of the above-described problem. An object of the present invention is to provide a novel material having high heat resistance which provides blue light emission, and a light-emitting element, a display apparatus, and an electronic appliance using the novel material.

A material of the present invention is a stilbene derivative represented by the following general formula (1). It is to be noted that X and Y, which are each a substituent represented by the following general formula (2) or (3) in the formula, may be the same or different from one another.

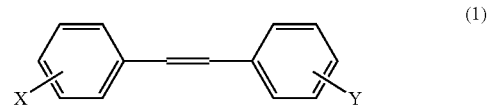

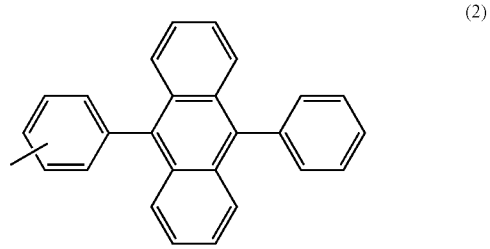

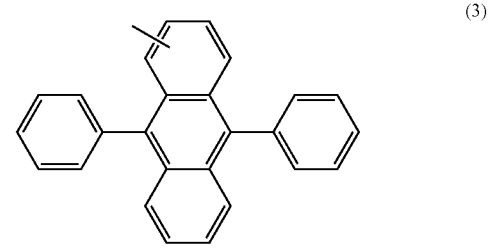

A material of the present invention is a stilbene derivative represented by the following general formula (1). It is to be noted that X and Y in the formula are each a substituent represented by the following general formula (2).

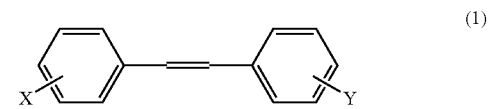

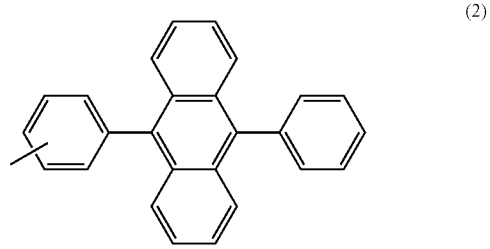

A material of the present invention is a stilbene derivative represented by the following general formula (1). It is to be noted that X and Y in the formula are each a substituent represented by the following general formula (3).

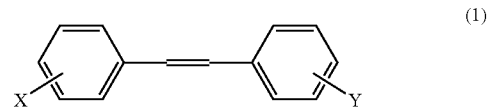

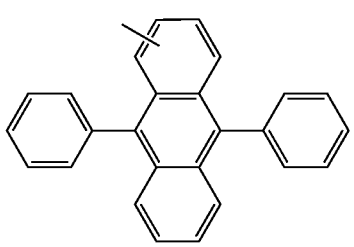

(3)

A material of the present invention is a stilbene derivative represented by the following general formula (1). It is to be noted that X in the formula is a substituent represented by the following general formula (2). Y in the formula is a substituent represented by the following general formula (3).

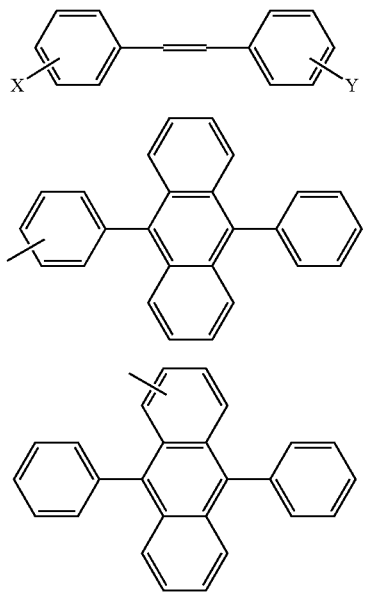

(1)

(2)

(3)

A material of the present invention is a stilbene derivative represented by the following structural formula (4).

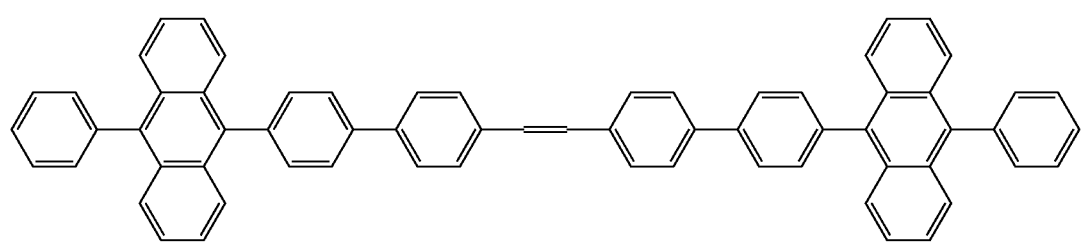

(4)

A feature of a material for a light-emitting element of the present invention is to contain any one of the above-described stilbene derivatives.

A light-emitting element of the present invention is characterized to include an organic material layer interposed between two electrodes. The organic material layer contains any one of the above-described stilbene derivatives.

A display apparatus of the present invention is characterized to include the above-described light-emitting element.

An electronic appliance of the present invention is characterized to include the above-described display apparatus.

The present invention can provide a blue light-emitting material. Further, the present invention can provide a light-emitting material of which the glass transition point is higher than that of a conventional blue light-emitting material using anthracene and stilbene by 40° C. or more. A material having a high glass transition point is excellent in heat resistance and reliability. Hence, the present invention can provide a blue light-emitting material having high heat resistance (high reliability). Moreover, a light-emitting element, a display apparatus, and an electronic appliance using the light-emitting material can be provided.

BRIEF DESCRIPTION OF THE DRAWINGS

In the accompanying drawings.

DETAILED DESCRIPTION OF THE INVENTION

Figure 1:
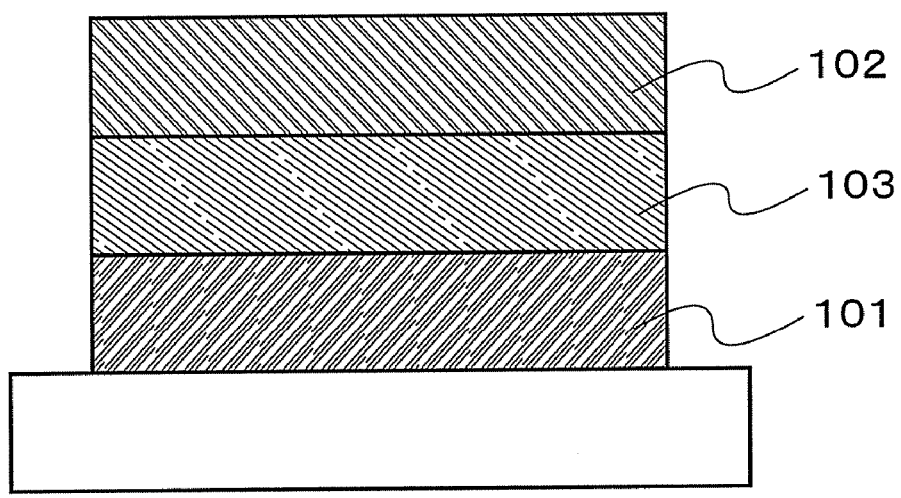
FIG. 1 illustrates a light-emitting element of the present invention.

Hereinafter, Embodiment Modes of the present invention will be described with reference to the accompanying drawings. It is to be noted that the present invention is not limited to the following description. It is easily understood by those skilled in the art that the modes and details can be variously changed without departing from the purpose and the scope of the present invention. Therefore, the present invention should not be interpreted as being limited to the descriptions of the embodiment modes below.

Embodiment Mode 1

A stilbene derivative of the present invention is represented by any one of the following general formulae (1), and (5) to (10).

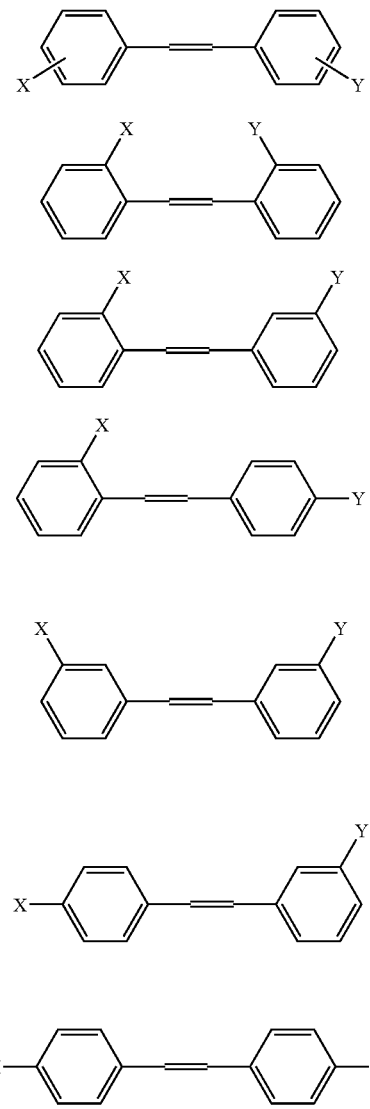

X in the above formulae is a substituent represented by any one of the following general formulae (2) and (3) and structural formulae (11) to (15).

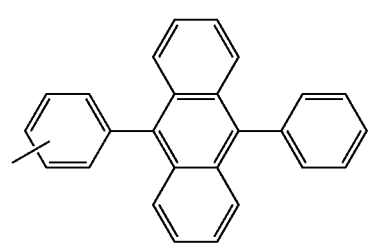

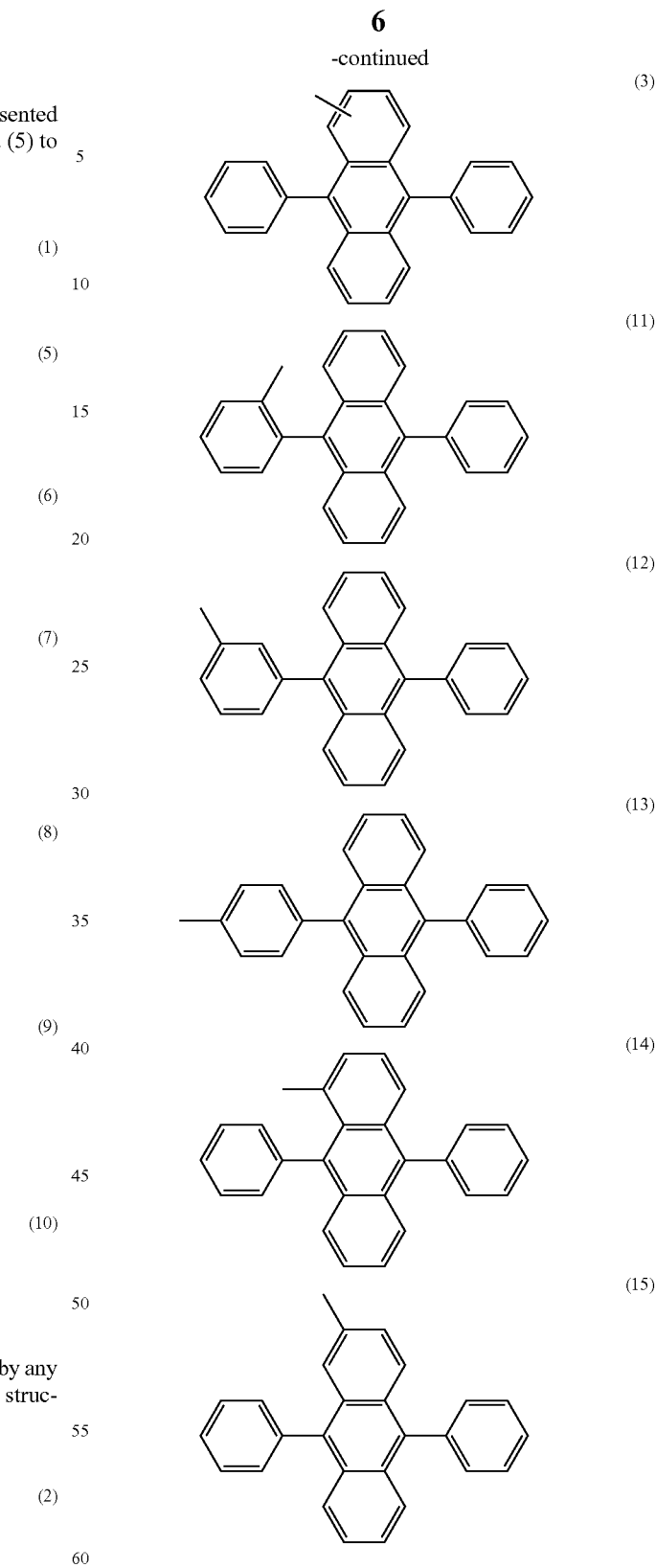

Y in the above formulae is a substituent represented by any one of the following general formulae (2) and (3) and structural formulae (11) to (15).

(2)
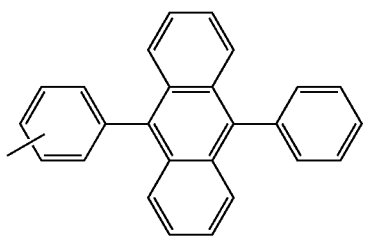

(13)
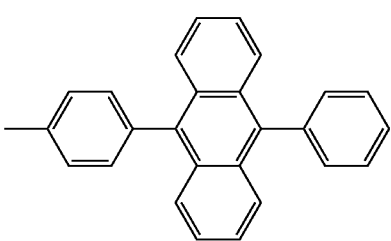

(3)
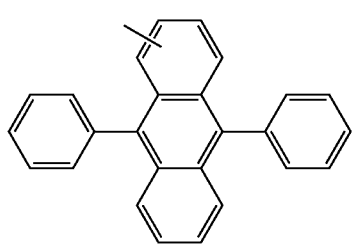

(14)
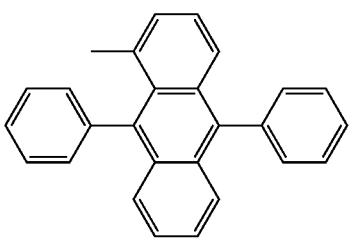

(11)
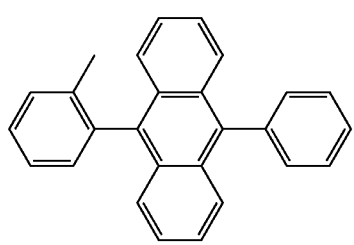

(15)
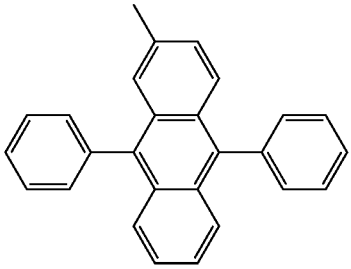

(12)
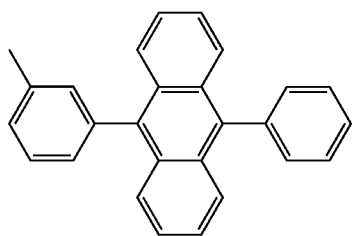

It is to be noted that X and Y may be the same or different from one another.

As the stilbene derivative of the present invention represented by any one of the above-described general formulae (1) to (13), a stilbene derivative represented by any one of the following structural formulae (16) to (116) can be given.

It is to be noted that the stilbene derivative of the present invention is not limited to those represented by any one of the following structural formulae (16) to (112) but includes all of those represented by general formulae (1) to (13).

(16)
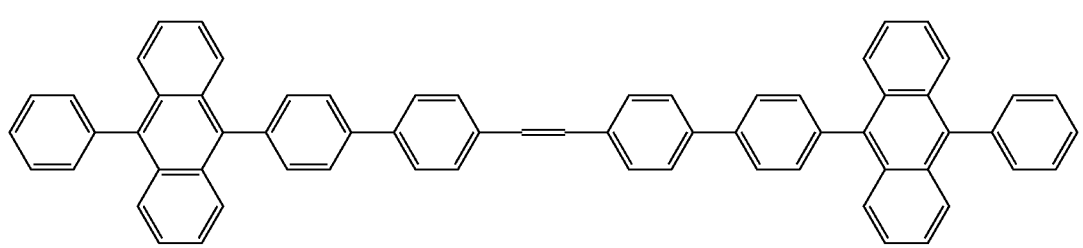

-continued
(17)
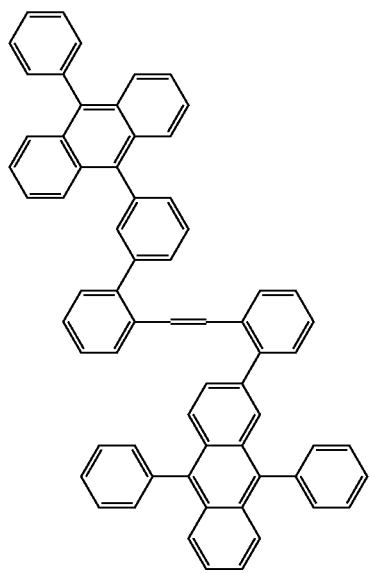
(18)
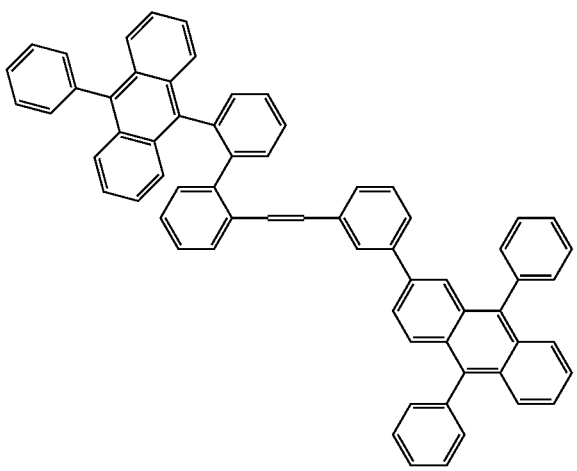
(19)
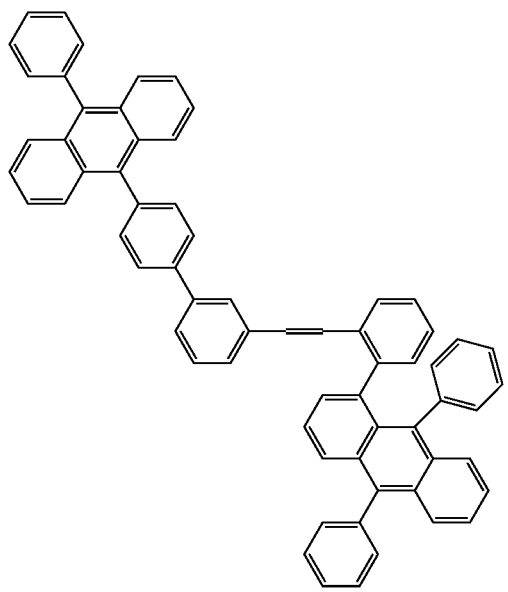
(20)
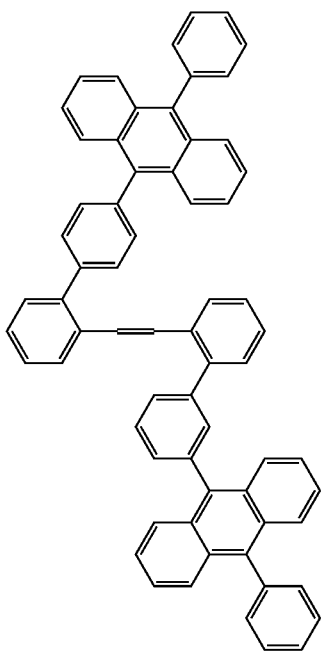
(21)
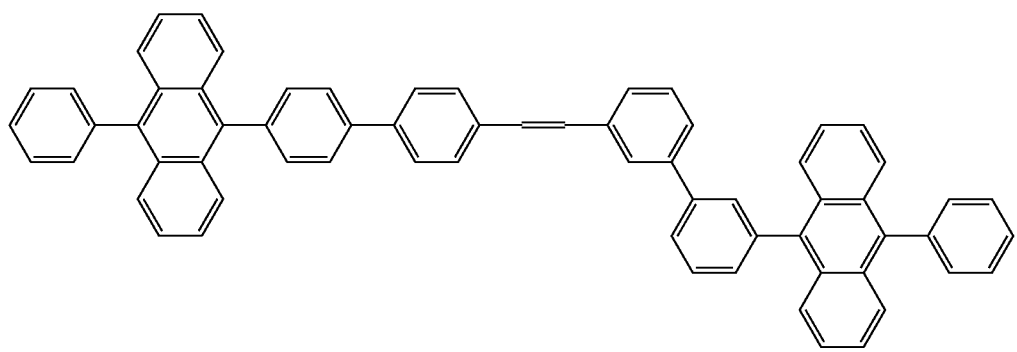

(22)
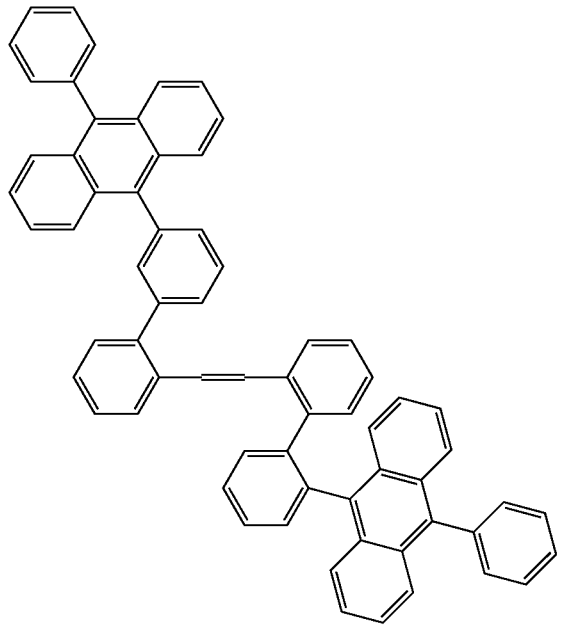
(23)
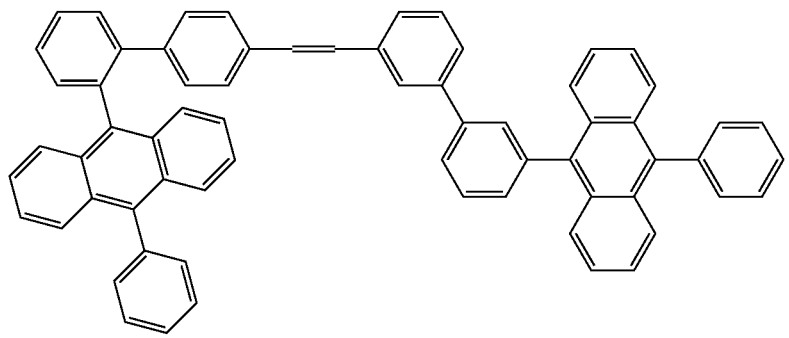
(24)
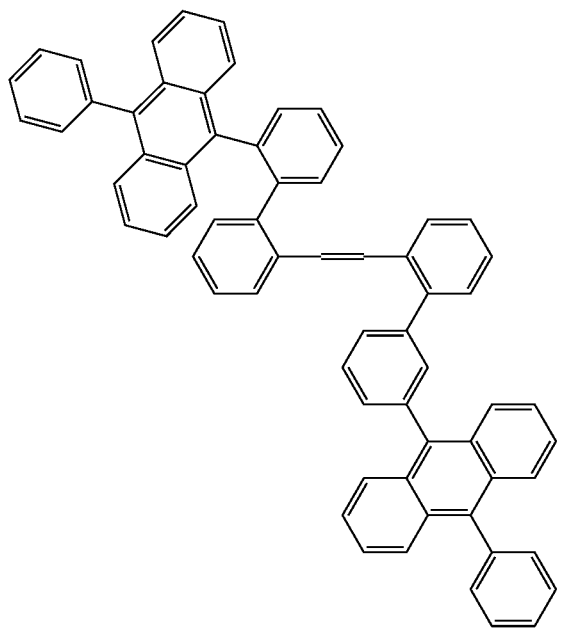
(25)
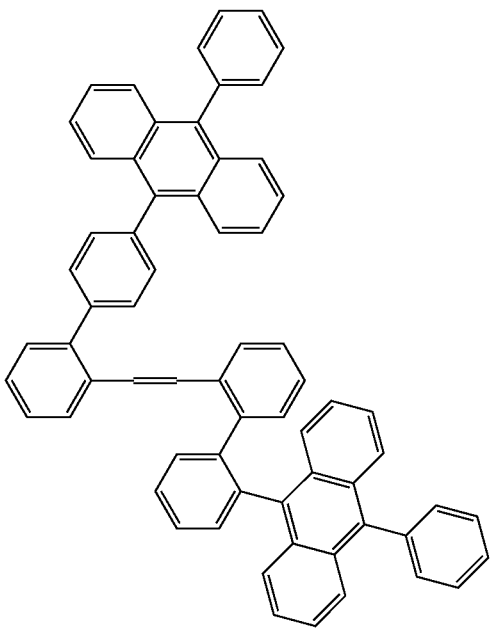

-continued
(26)
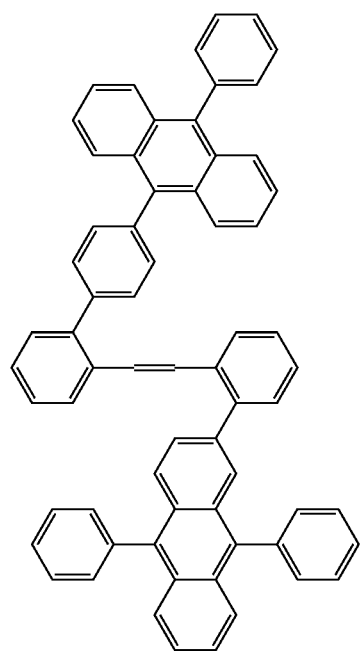
(27)
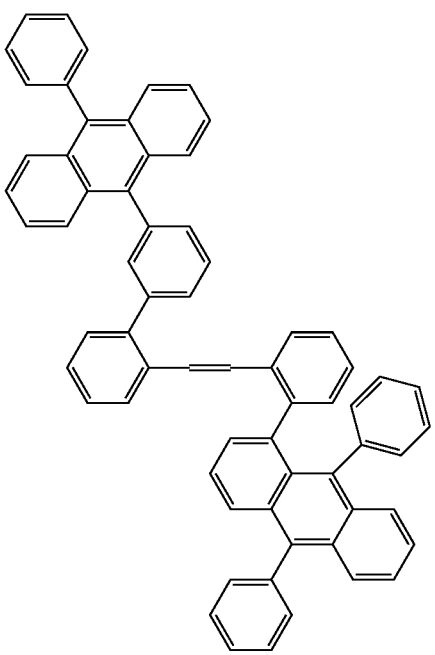
(28)
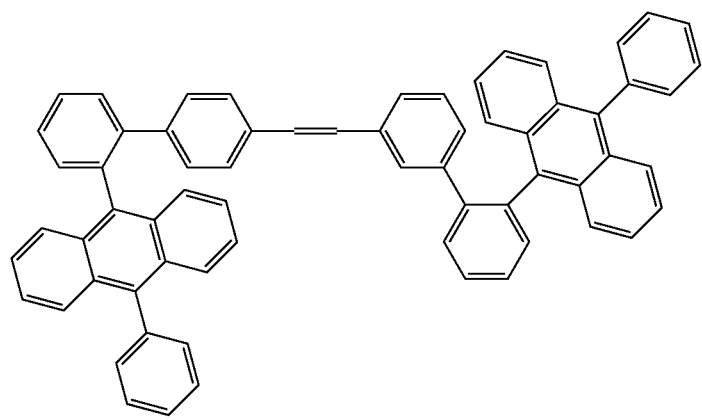
(29)
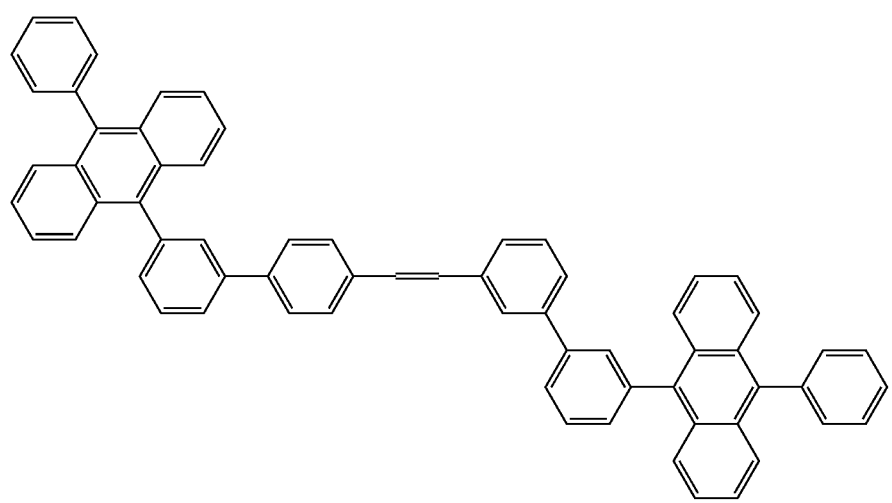

-continued
(30)
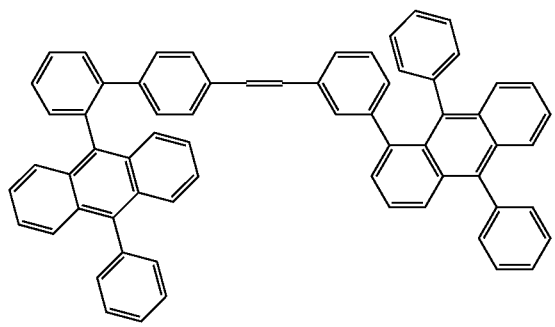
(31)
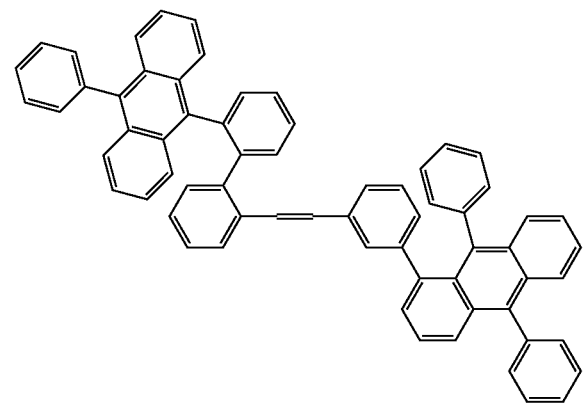
(32)
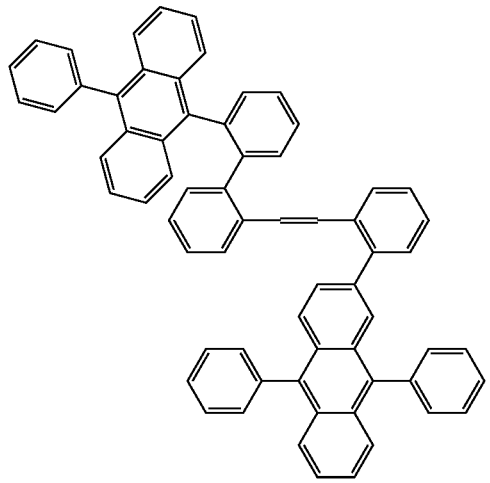
(33)
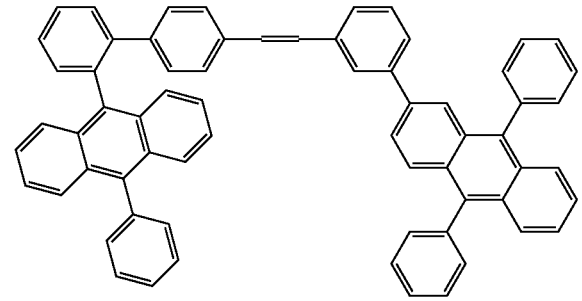
(34)
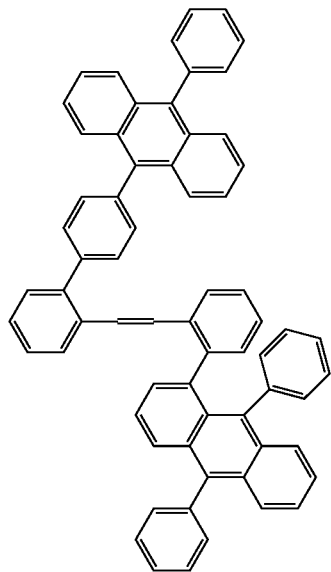
(35)
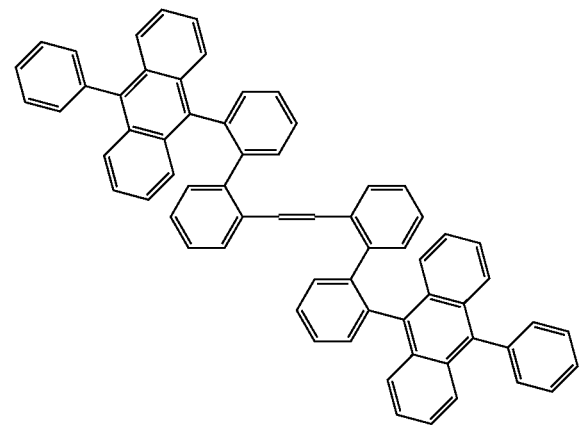

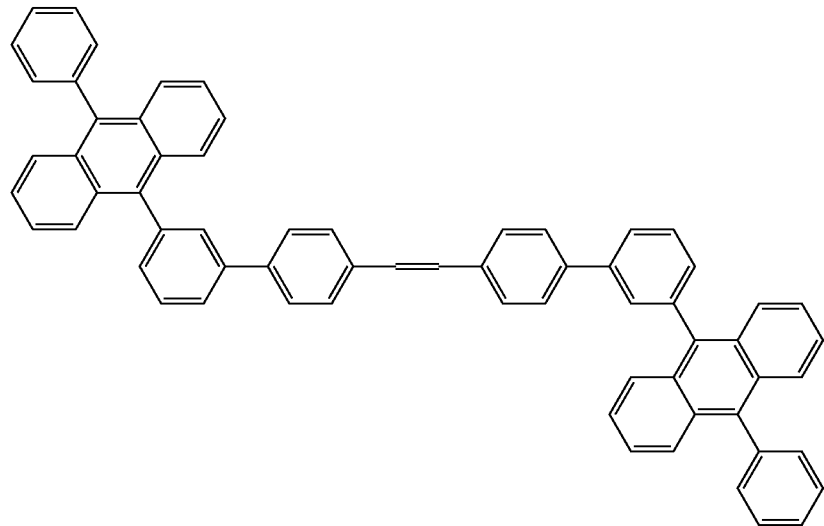
(36)
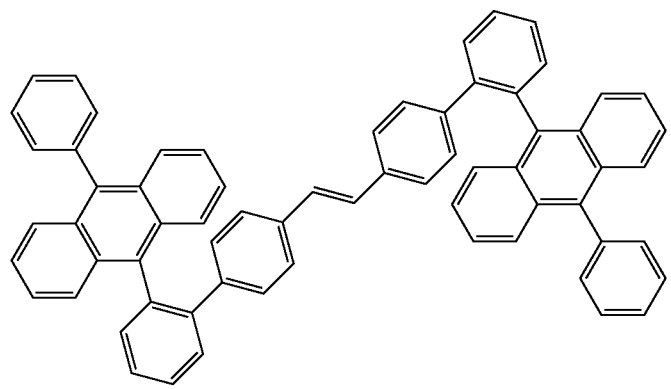
(37)
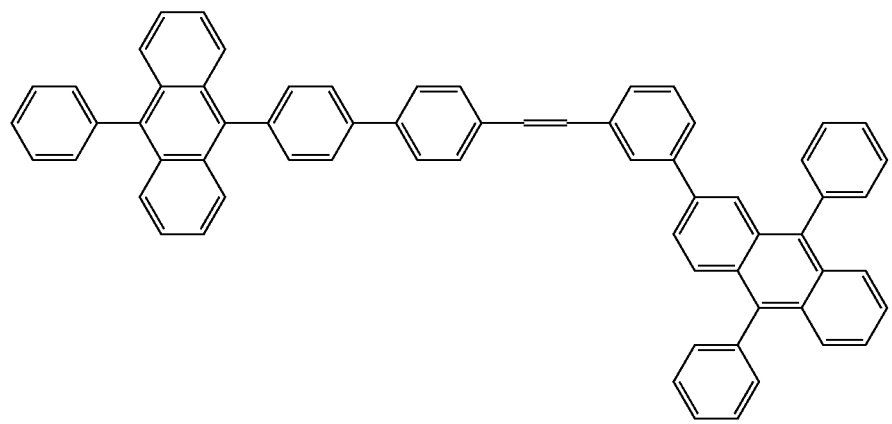
(38)

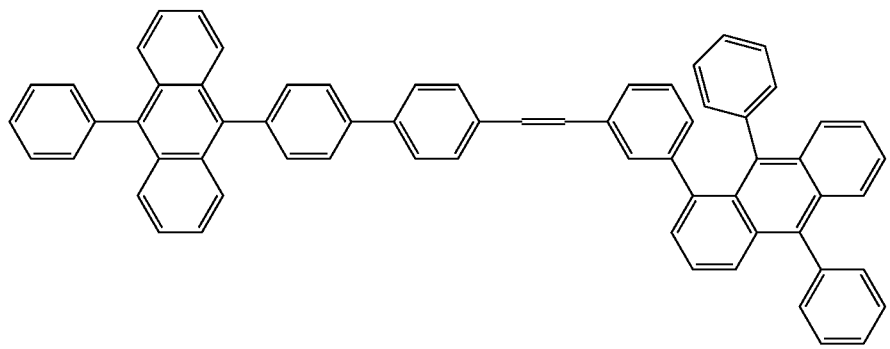
(39)
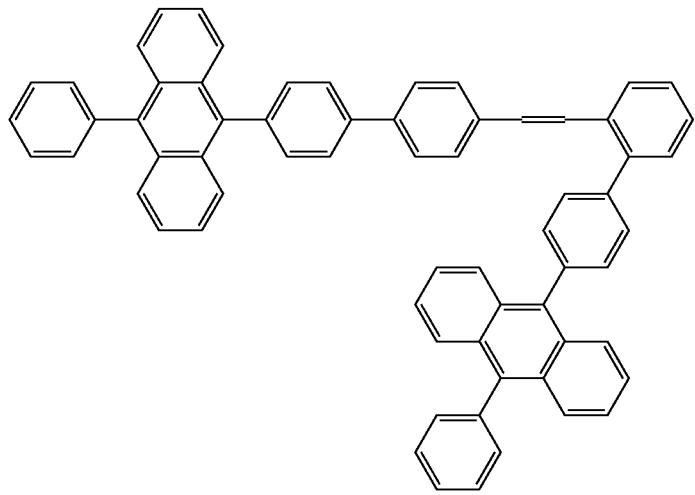
(40)
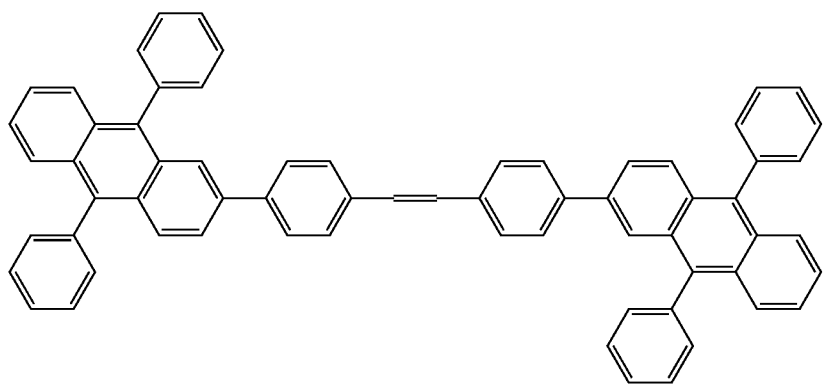
(41)
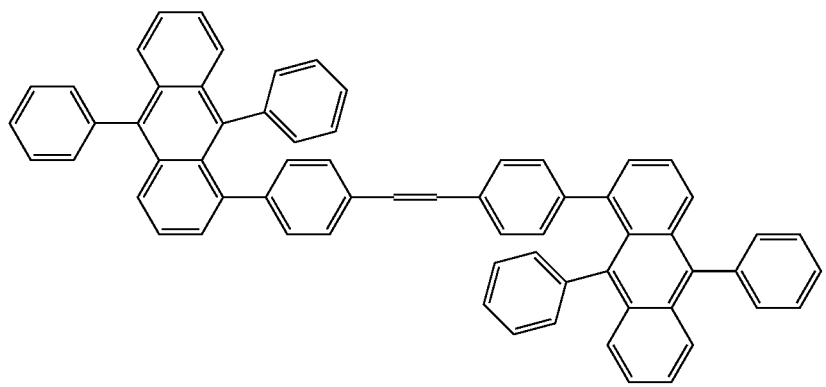
(42)

(43)
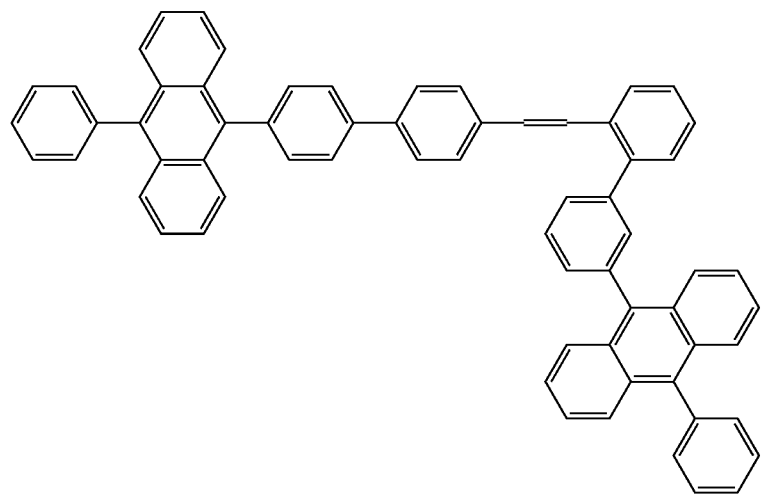
(44)
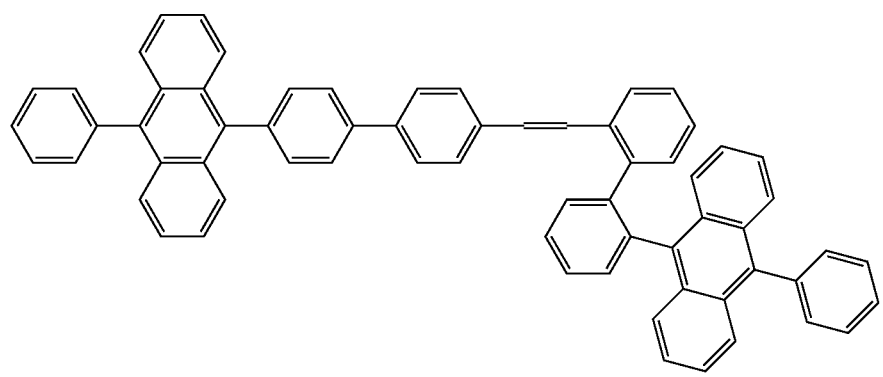
(45) (46)
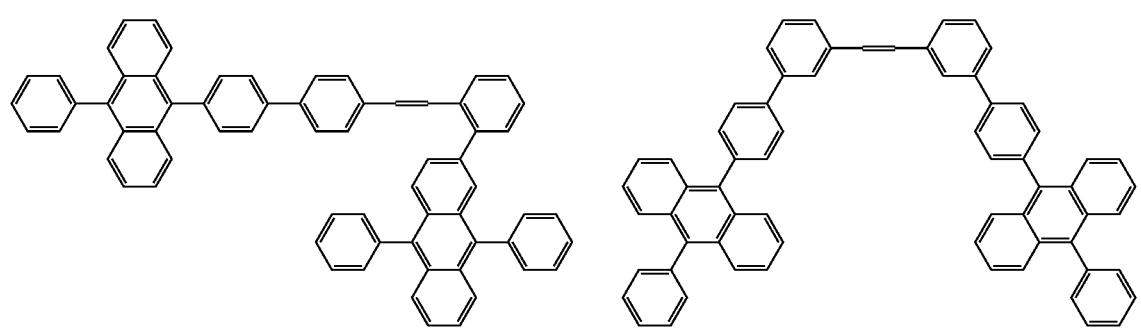
(47)
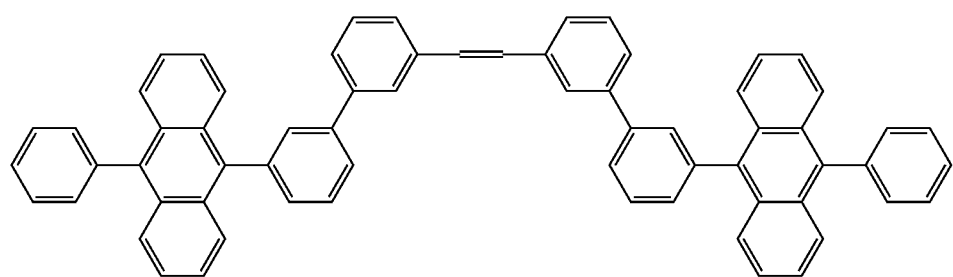

-continued
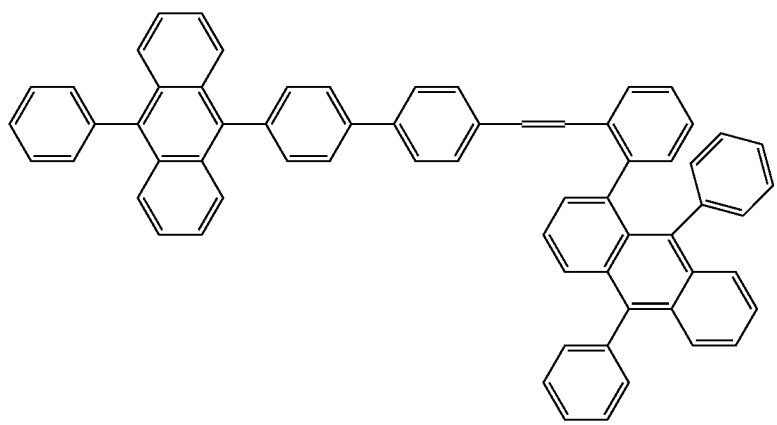
(48)
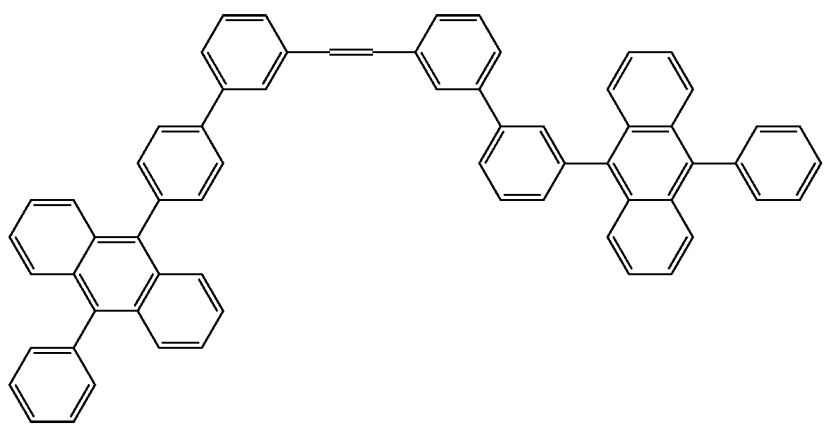
(49)
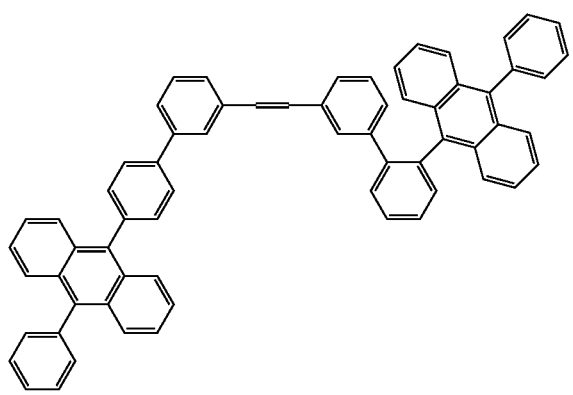
(50)
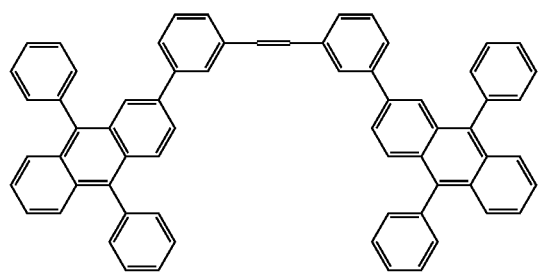
(51)
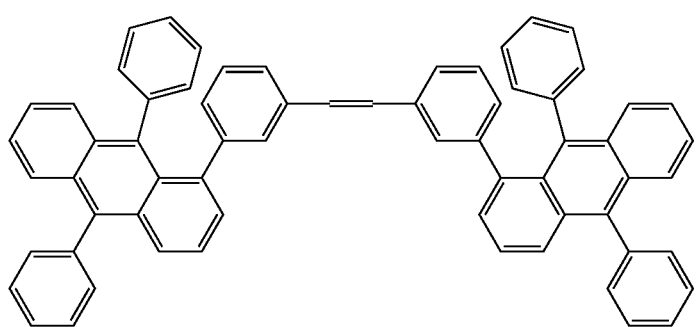
(52)

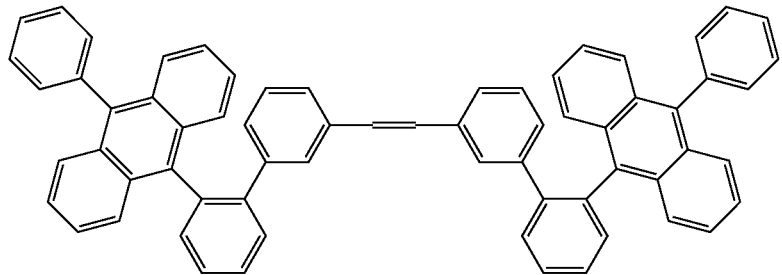
(53)
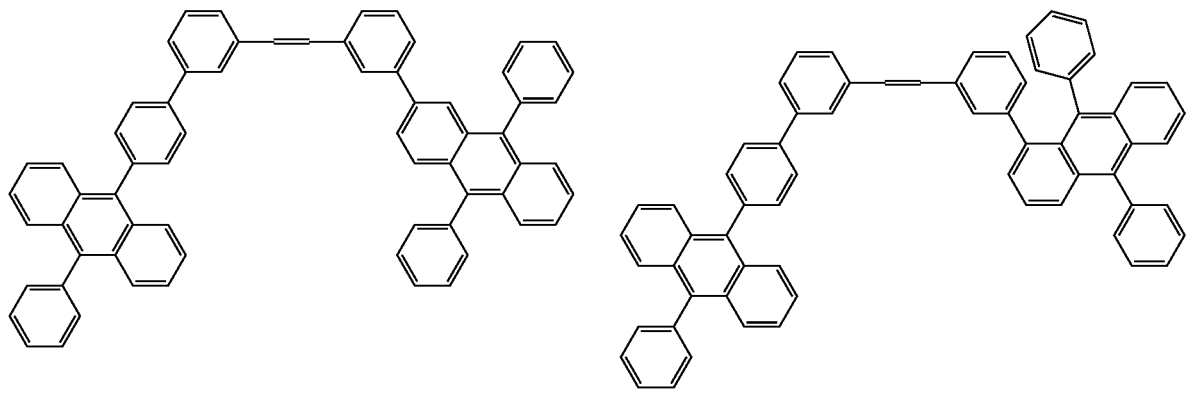
(54)
(55)
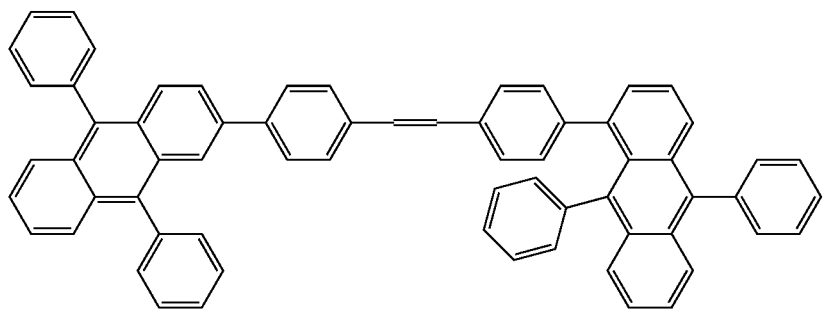
(56)
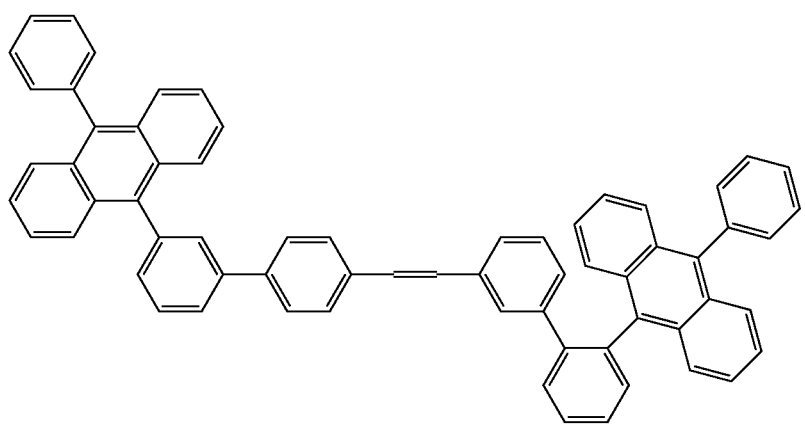
(57)

(58)
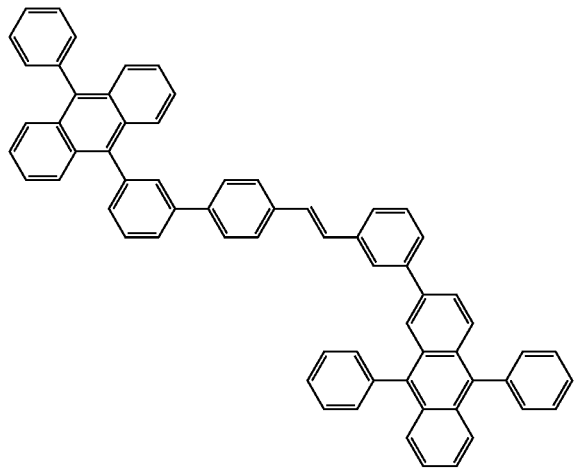
(59)
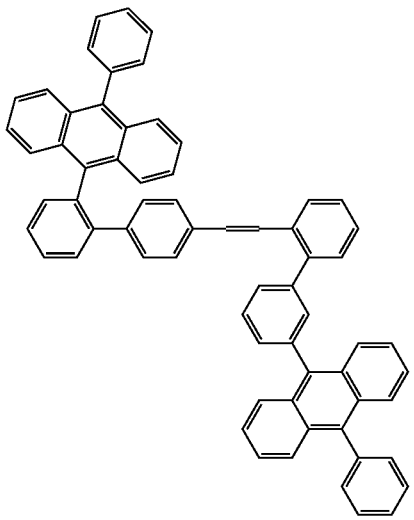
(60)
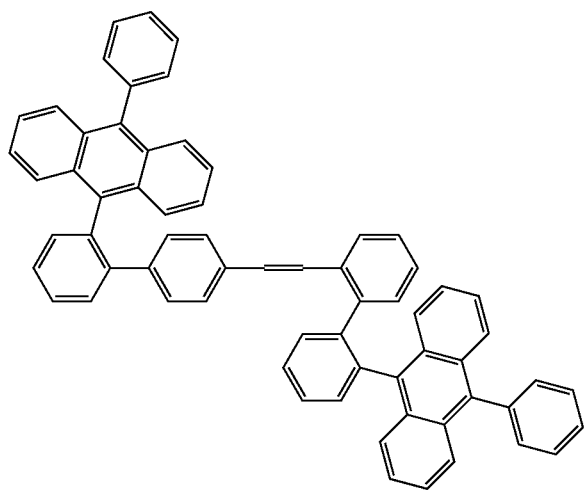
(61)
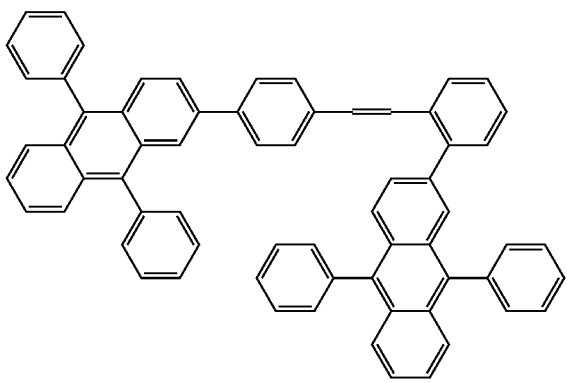
(62)
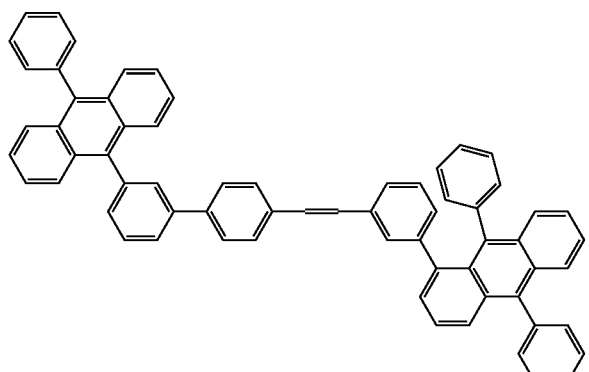
(63)
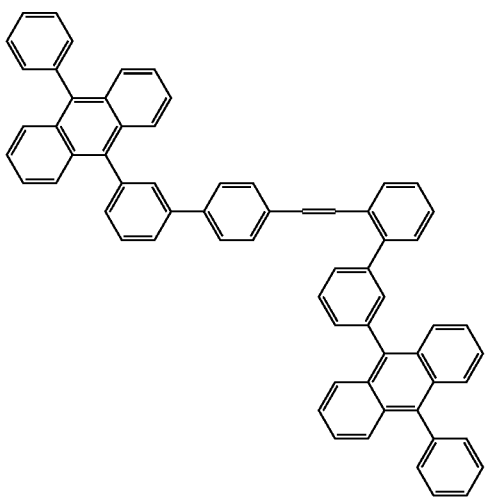

-continued
(64)
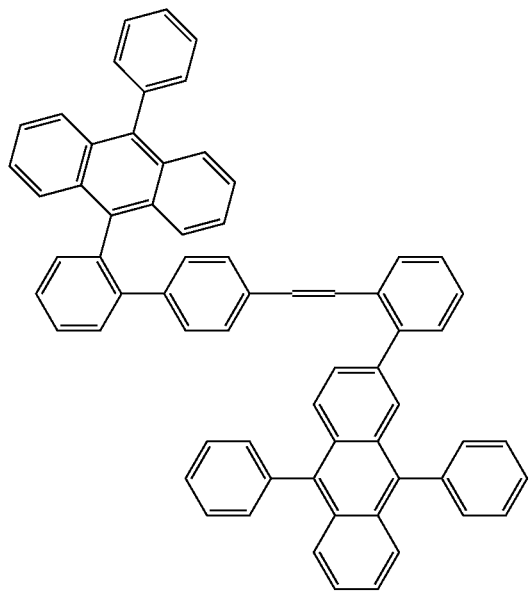
(65)
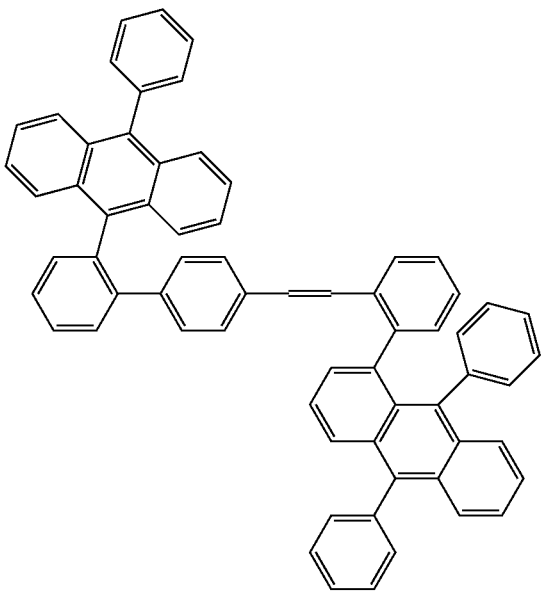
(66)
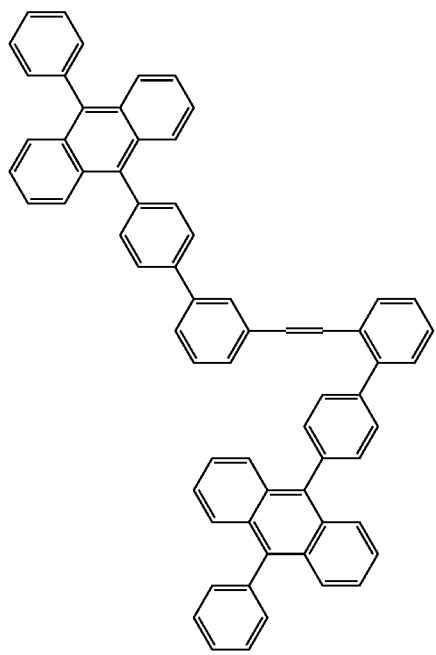
(67)
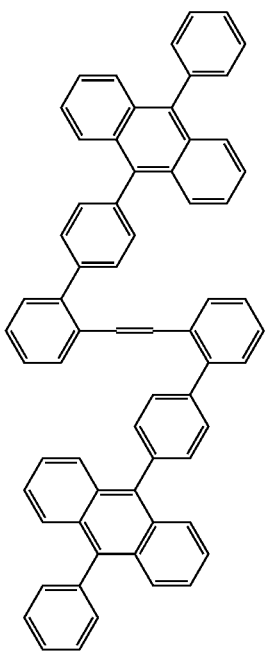

-continued
(68)
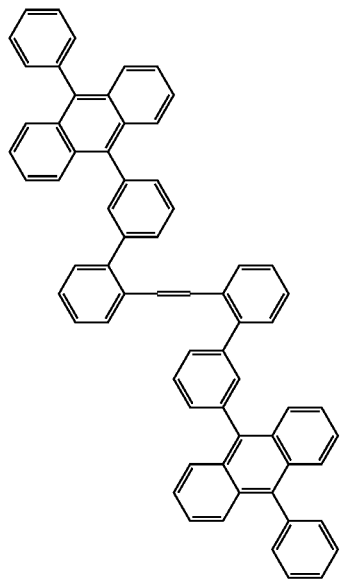
(69)
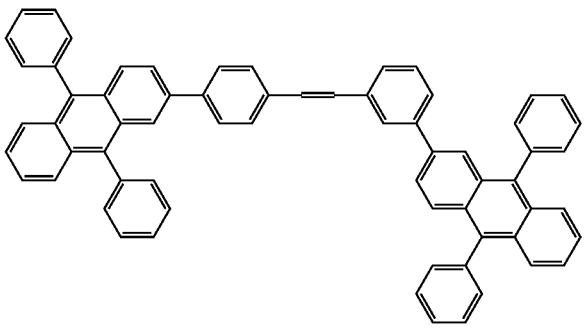
(70)
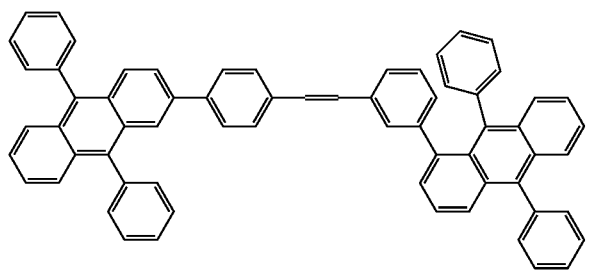
(71)
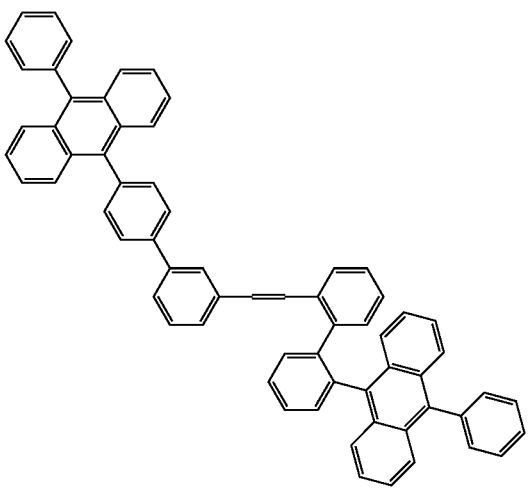
(72)
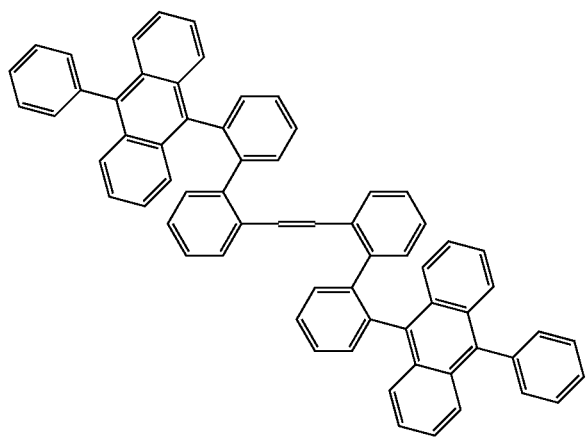
(73)
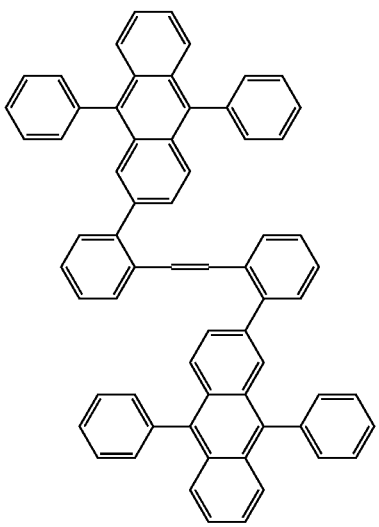

-continued
(74)
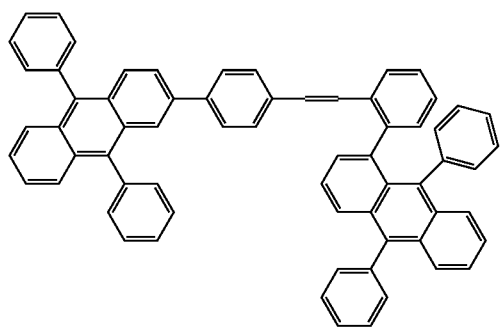
(75)
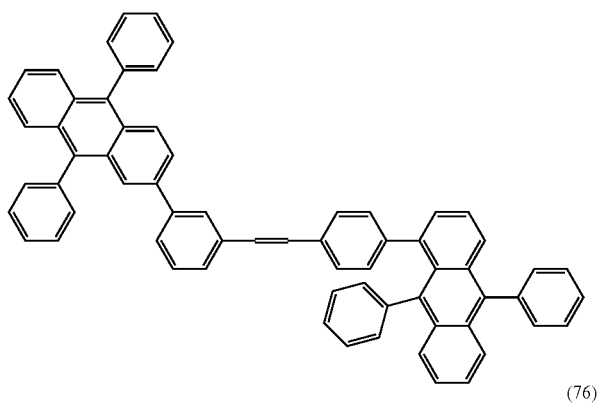
(76)
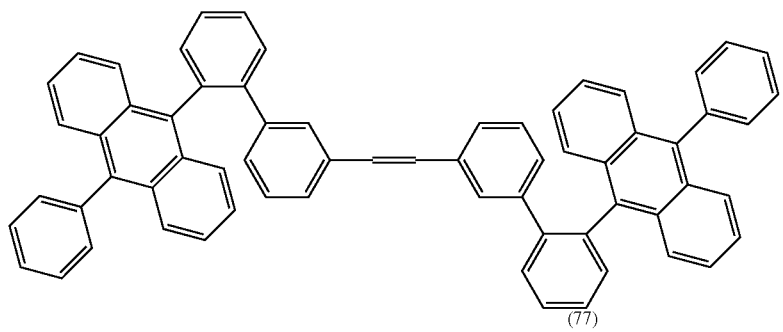
(77)
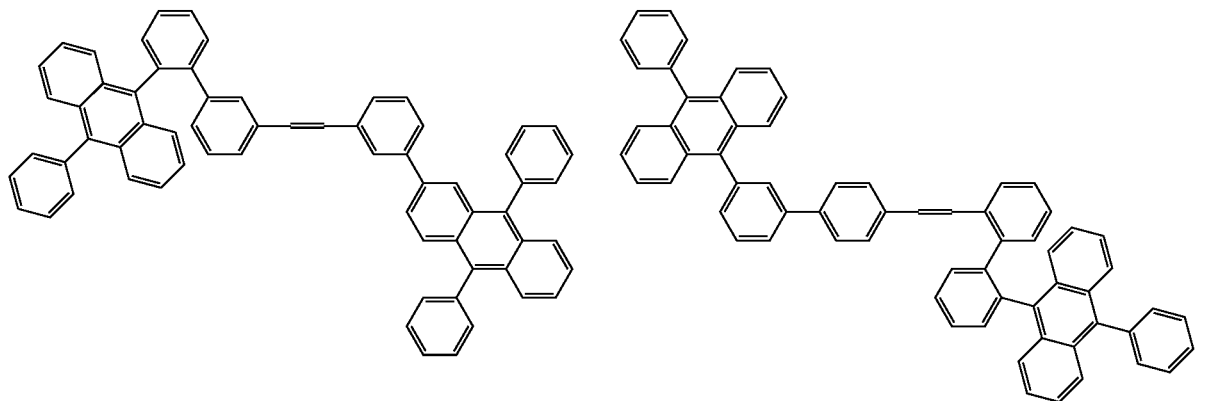
(78)
(79)
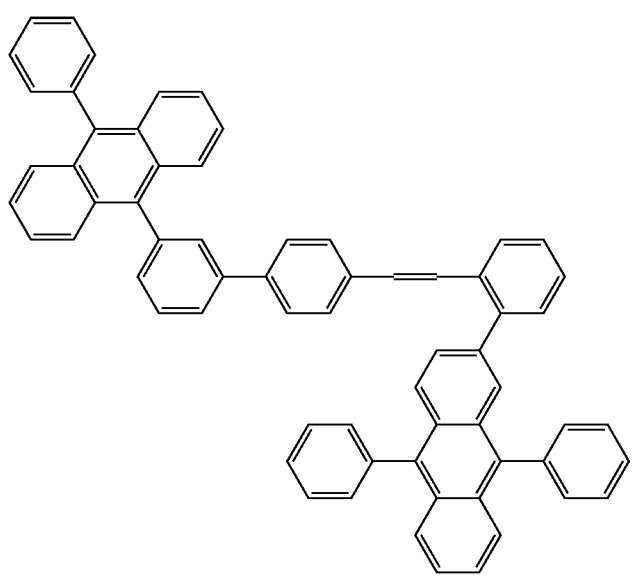

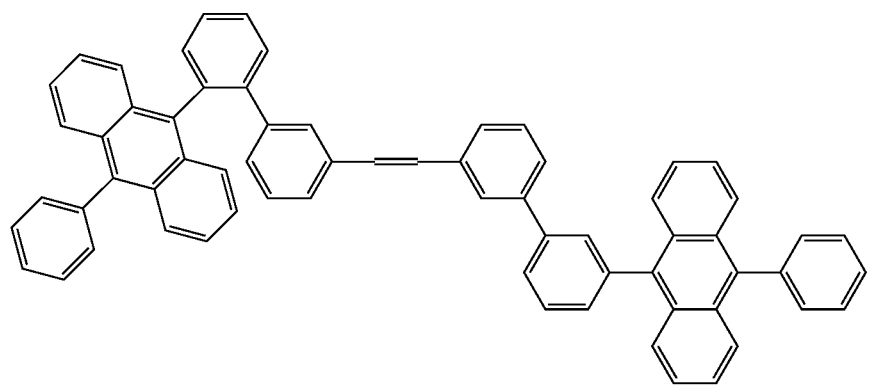
(80)
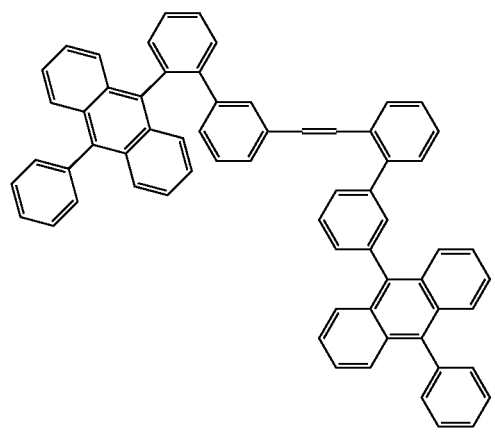
(81)
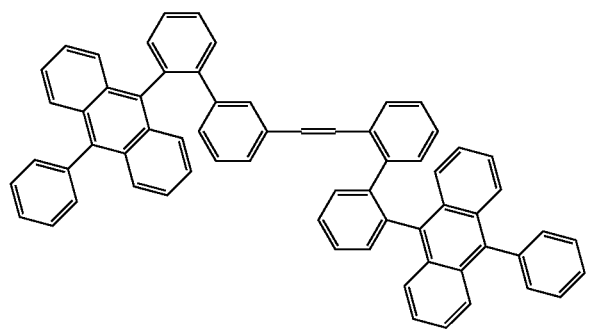
(82)
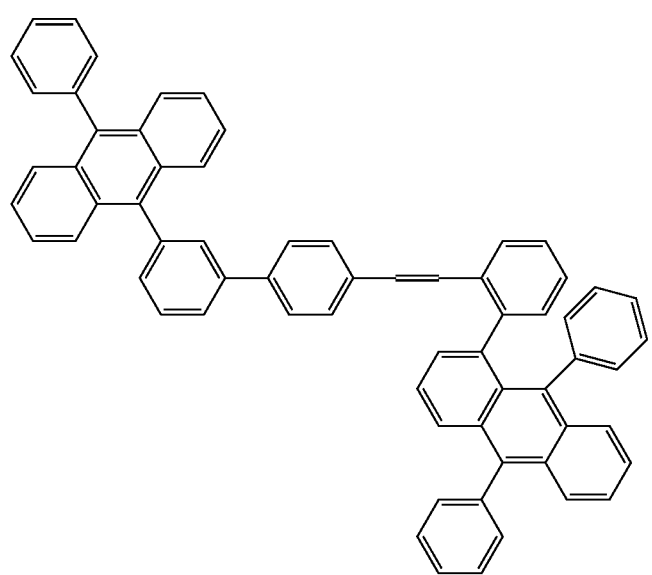
(83)

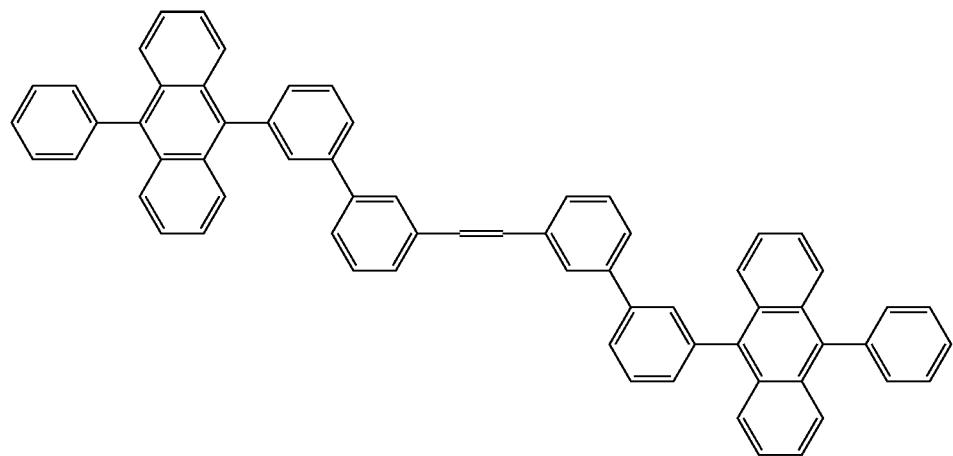
(84)
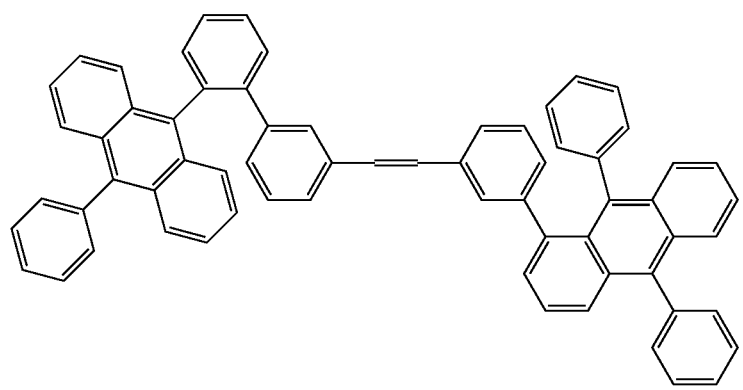
(85)
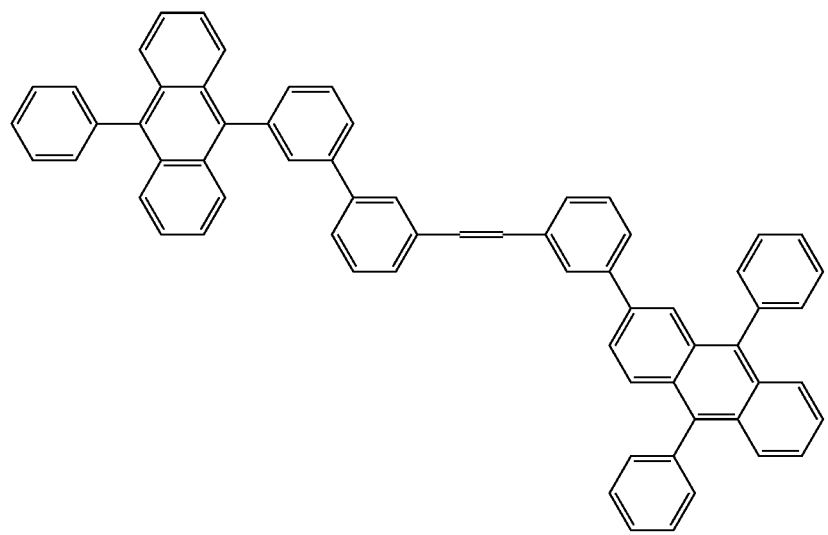
(86)

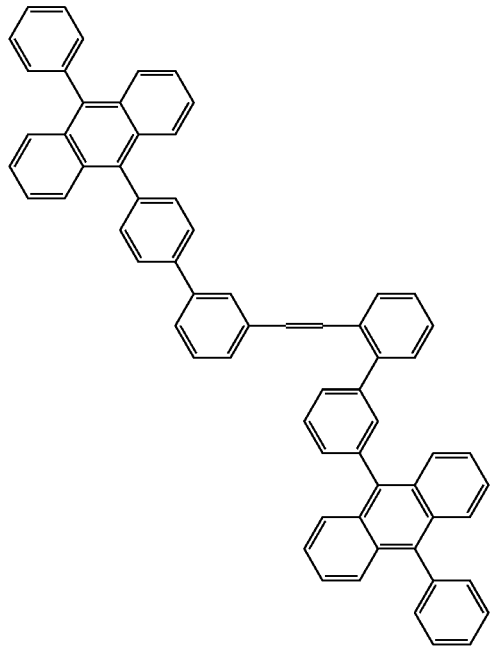
(87)
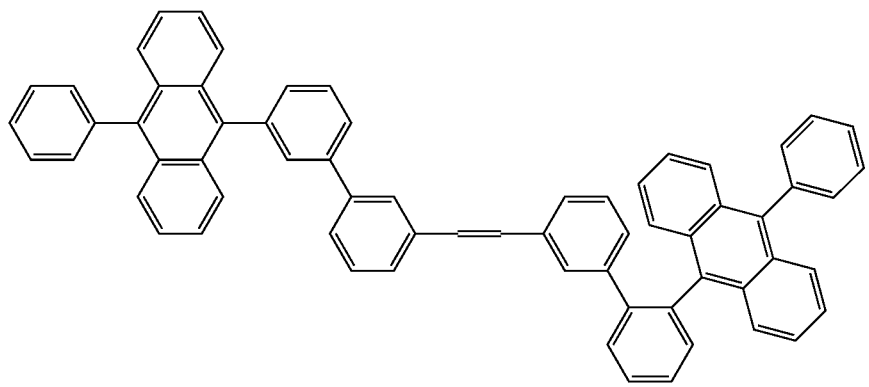
(88)
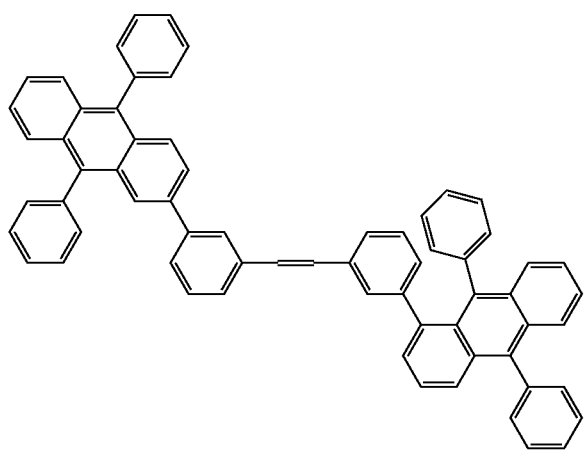
(89)
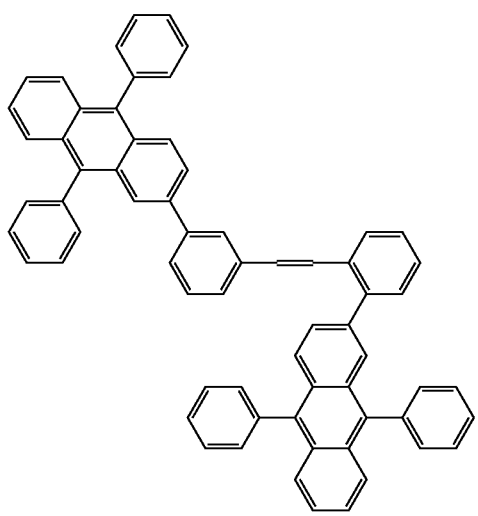
(90)

-continued
(91)
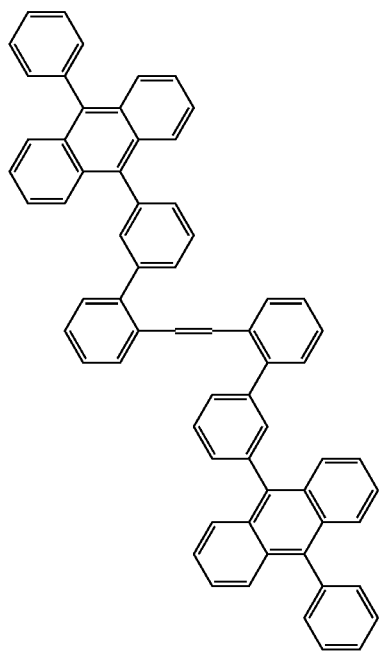
(92)
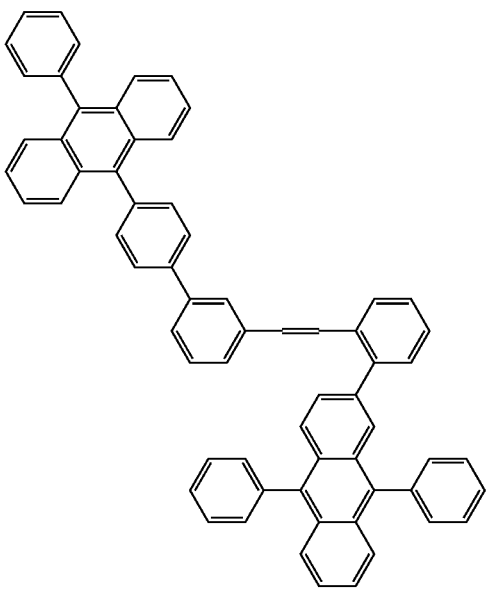
(93)
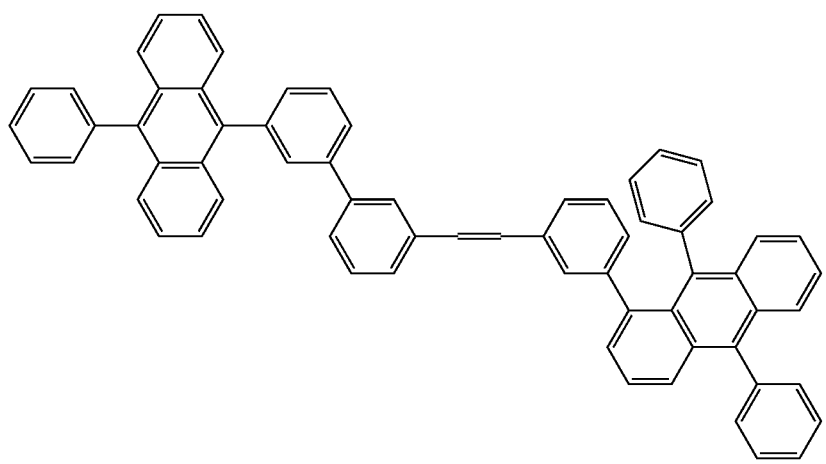
(94)
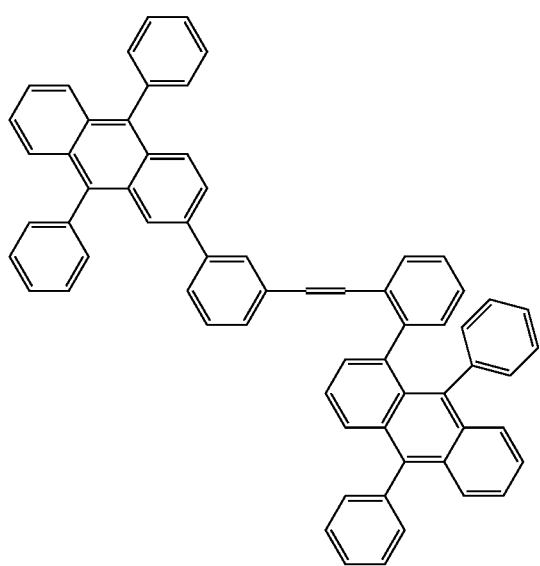
(95)
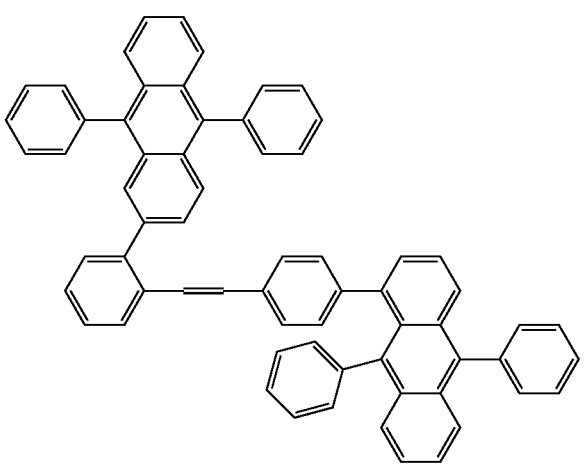

-continued
(96)
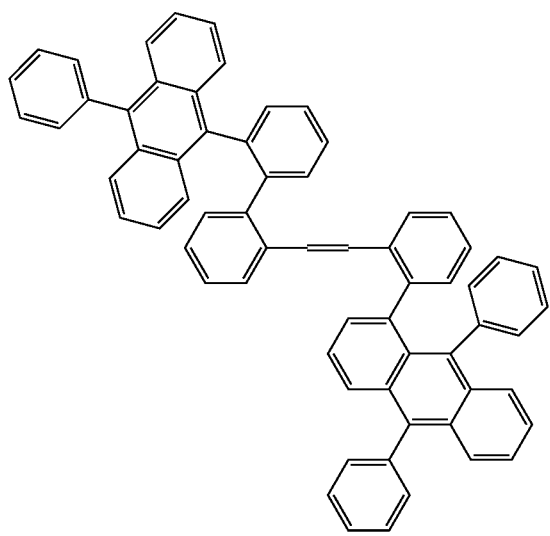
(97)
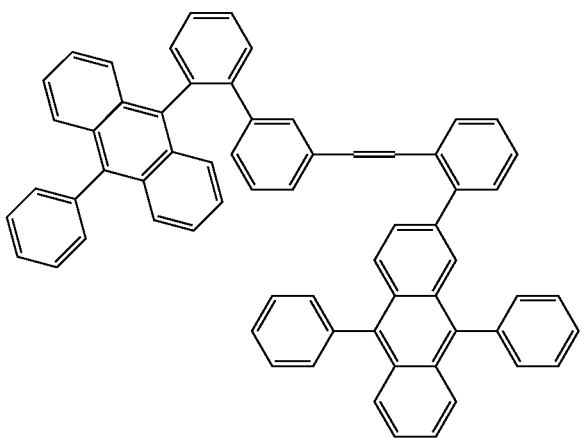
(98)
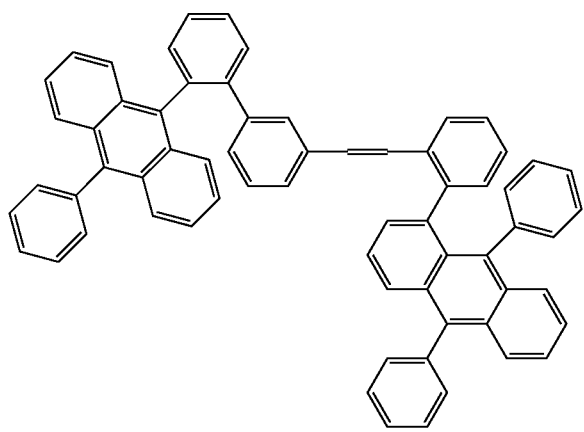
(99)
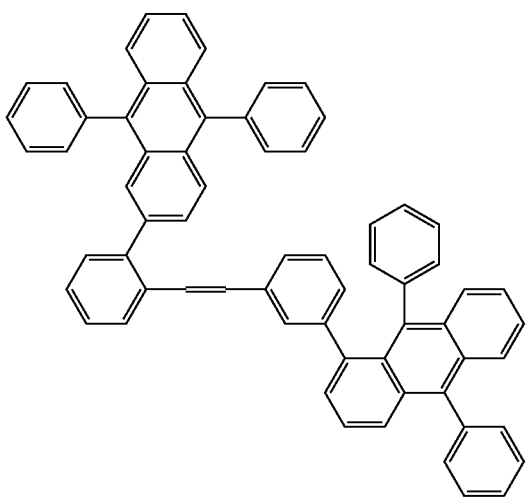
(100)
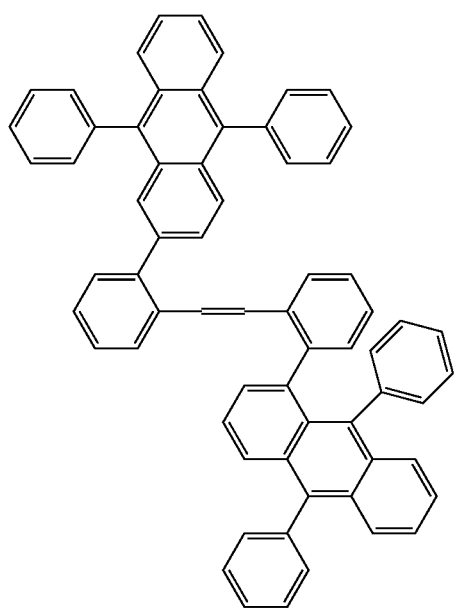

(101)
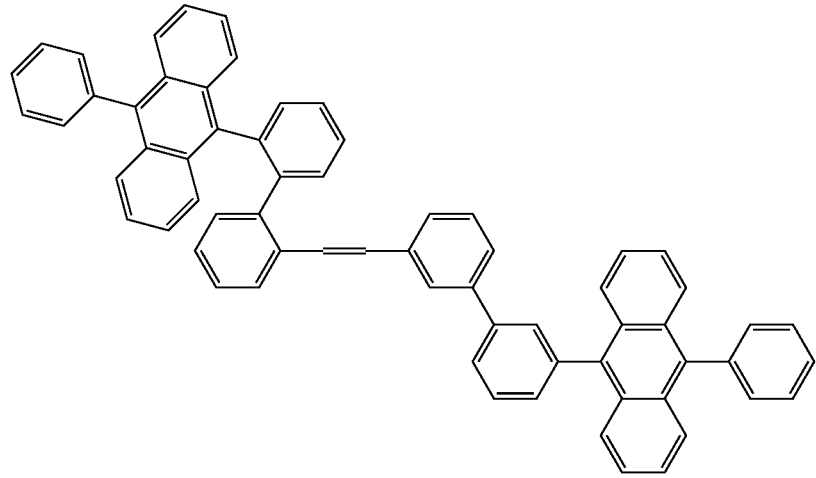
(102)
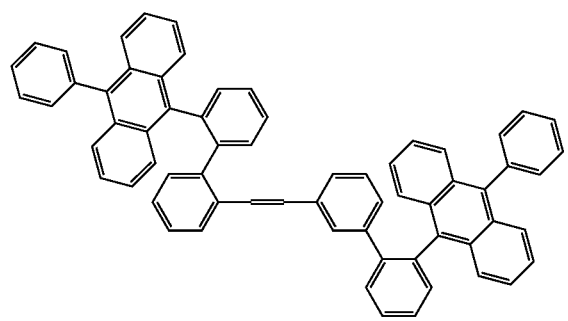
(103)
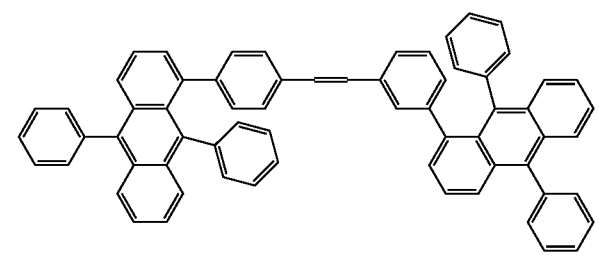
(104)
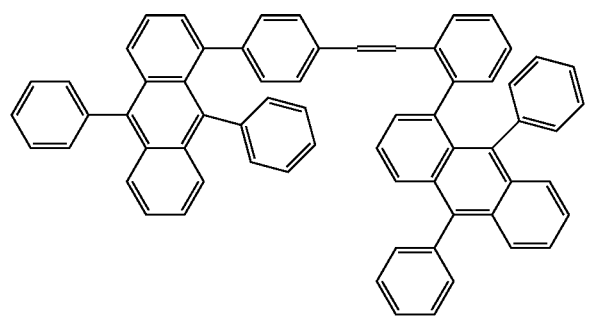
(105)
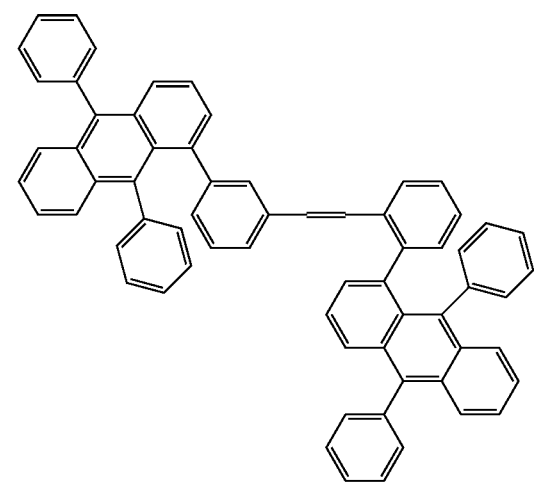

(106)
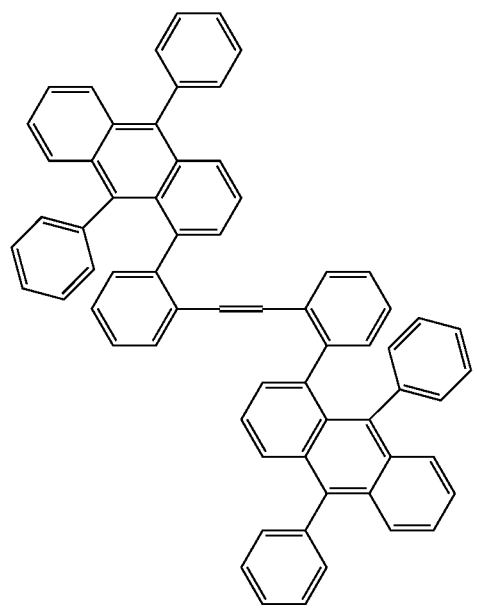
(107)
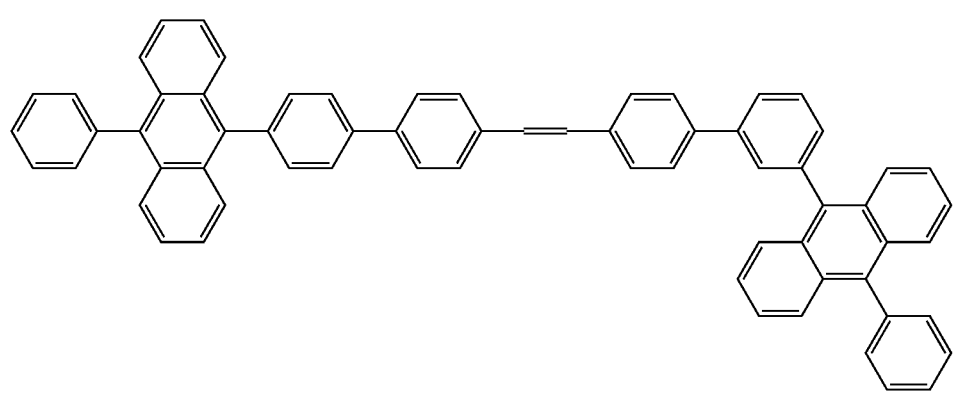
(108)
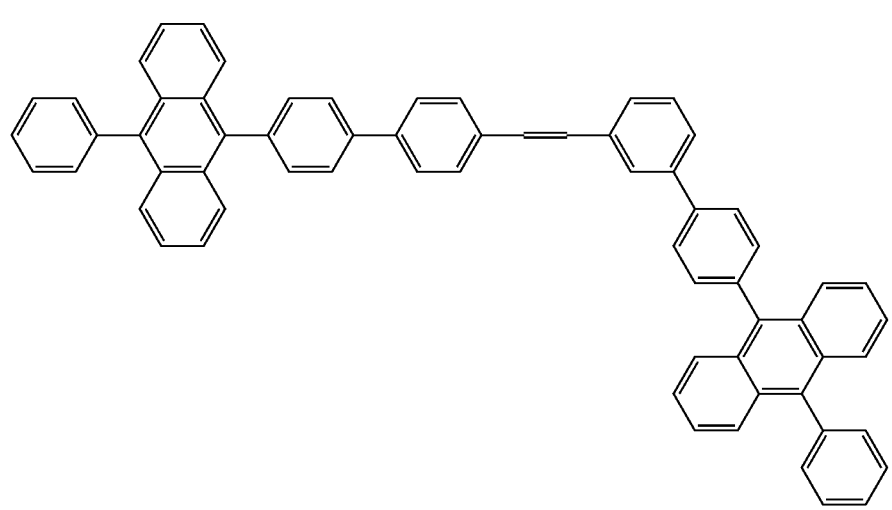

-continued

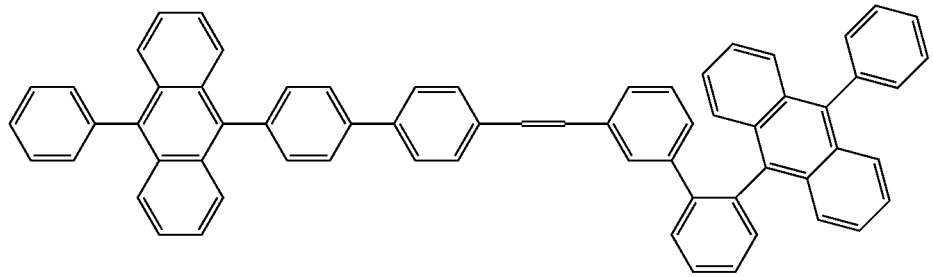

(109)

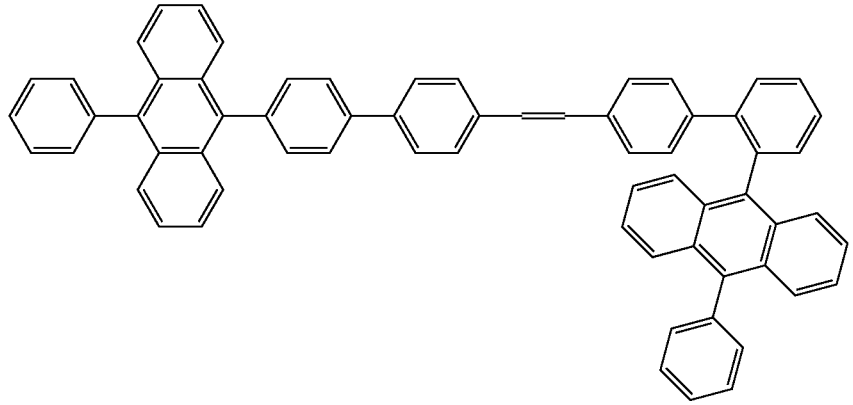

(110)

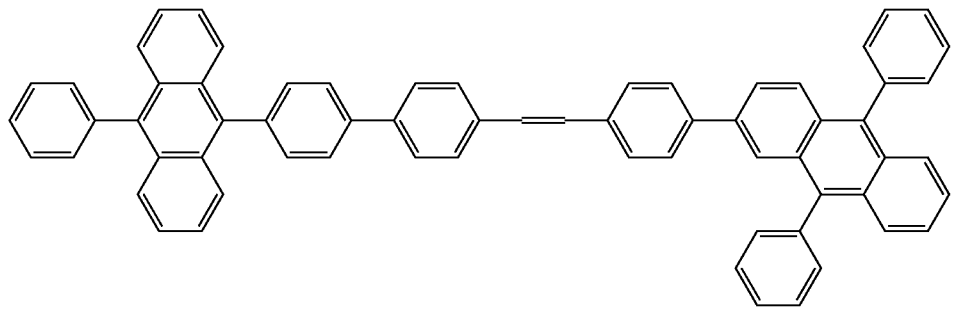

(111)

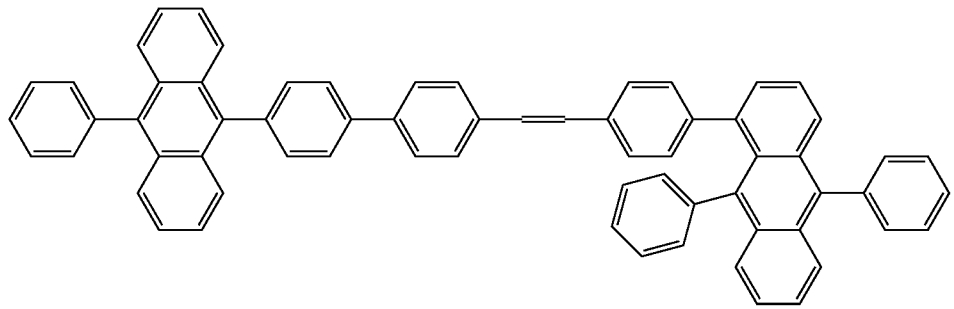

(112)

The stilbene derivative of the present invention is characterized in that blue light emission can be obtained therefrom.

Embodiment Mode 2

A method for synthesizing the stilbene derivative of the present invention represented by the general formula (1) is described below.

[Step 1: Synthesis of a Halogenated Stilbene Derivative (St1)]

As illustrated in the following synthetic scheme (A), triphenylphosphonium salt (α1) of a benzyl derivative whose benzene ring is halogenated and benzaldehyde (β1) whose benzene ring is halogenated are reacted in the presence of a base to obtain a dihalogenated stilbene derivative (St1) whose benzene ring is halogenated (so-called Wittig reaction). As illustrated in synthetic scheme (A'), this dihalogenated stilbene derivative (St1) can also be obtained by using phosphonate ester (α2) instead of the triphenylphosphonium salt (α1) (so-called Horner-Emmons reaction).

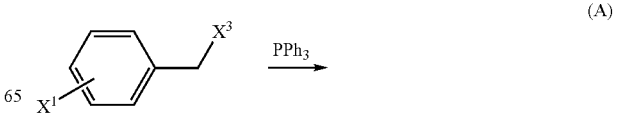

(A)

-continued

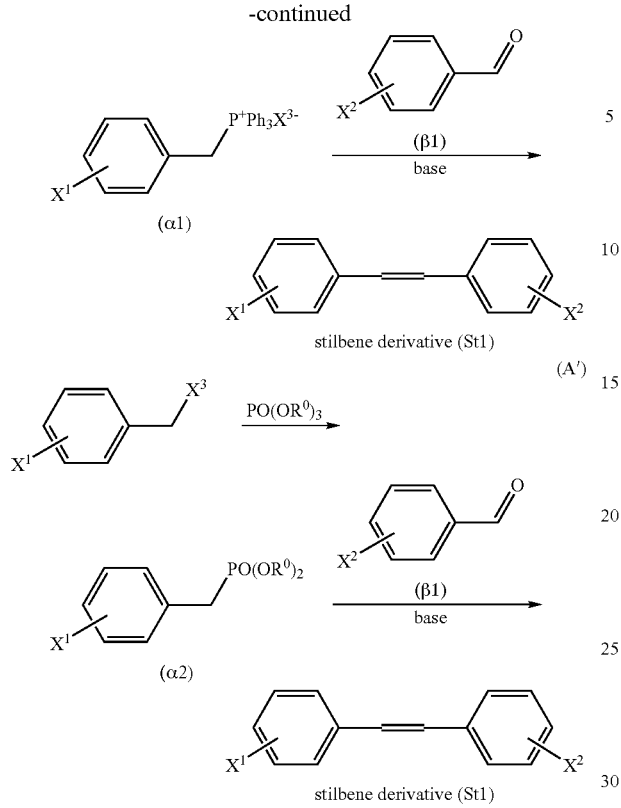

$X^1, X^2, X^3$ = halogen (bromine or iodine is preferable)
$R^0$ = alkyl Group

[Step 2: Synthesis of a Stilbene Derivative of the Present Invention Represented by General Formula (1)]

Next, as illustrated in the following synthetic scheme (B), a halogenated stilbene derivative (St1) and a boronic acid derivative or an organoboron compound are coupled with each other in the presence of a base by using a metal catalyst to obtain a stilbene derivative of the present invention represented by the general formula (1). As the metal catalyst, a palladium catalyst such as palladium(II) acetate or tetrakis (triphenylphosphine)palladium(0) can be used. As the base, an inorganic salt such as potassium carbonate or sodium carbonate, or an organic base such as sodium-tert-butoxide (abbreviation: tert-BuONa) or potassium-tert-butoxide can be used. As halogen, bromine or iodine is preferable.

R1, R2: hydrogen or alkyl group having 1 to 10 carbon atoms
R1 and R2 may form a ring by comobining to each other when R1 and R2 are alkyl groups X in the above formula is a substituent represented by the following general formula (2) or (3).

Y in the above formulae is a substituent represented by the following general formula (2) or (3).

Embodiment Mode 3

In accordance with the present invention, a light-emitting element can be formed using the stilbene derivative illustrated in Embodiment Mode 1.

A light-emitting element of the present invention has an element structure in which a layer 103 containing a light-emitting substance is interposed between a first electrode 101 and a second electrode 102 as illustrated in FIG. 1. A stilbene derivative of the present invention is contained in the layer 103 containing a light-emitting substance. Here, a case is described in which the first electrode 101 serves as an anode and the second electrode 102 serves as a cathode. It is to be noted that holes are injected from the anode into the layer 103 containing a light-emitting substance and electrons are injected from the cathode into the layer 103 containing a light-emitting substance.

The layer 103 containing a light-emitting substance has a stacked-layer structure including at least a light-emitting layer. The following structures can be given as examples: a stacked-layer structure of a hole injecting layer, a light-emitting layer, and an electron transporting layer in this order; a stacked-layer structure of a hole injecting layer, a hole transporting layer, a light-emitting layer, and an electron transporting layer in this order; a stacked-layer structure of a hole injecting layer, a hole transporting layer, a light-emitting layer, a hole-blocking layer, and an electron transporting layer in this order; a stacked-layer structure of a hole injecting layer, a hole transporting layer, a light-emitting layer, a hole-blocking layer, an electron transporting layer, and an electron injecting layer in this order; and the like.

The light-emitting element of the present invention is formed preferably over a substrate. The substrate can be formed of glass, quartz, transparent plastic, or the like.

For the layer 103 containing a light-emitting substance, known materials can be used. For example, either a low molecular compound or a high molecular compound can be used. It is to be noted that not only an organic compound material but also a material containing an inorganic compound may be used for the layer 103 containing a light-emitting substance.

It is to be noted that the layer 103 containing a light-emitting substance is formed by stacking layers such as a hole injecting layer formed of a hole injecting substance; a hole transporting layer formed of a hole transporting substance or a bipolar substance; a light-emitting layer formed of a light-emitting substance; a hole blocking layer formed of a hole blocking substance; an electron transporting layer formed of an electron transporting substance; an electron injecting layer formed of an electron injecting substance; a first buffer layer; or a second buffer layer.

In the case of using a stilbene derivative for the layer 103 containing a light-emitting substance in the present invention, the stilbene derivative of the present invention is used for either the light-emitting layer or another layer (e.g., the hole injecting layer, the hole transporting layer, the hole blocking layer, the electron transporting layer, the electron injecting layer, the first buffer layer, or the second buffer layer). Then, the light-emitting layer and another layer, one of which contains the stilbene derivative of the present invention, are stacked; thus, a light-emitting element can be formed. Materials used for these layers will be specifically described below.

As an anode material for the light-emitting element of the present invention, a substance having a high work function (work function of greater than or equal to 4.0 eV) is preferable (e.g., a metal, an alloy, a conductive compound, or a mixture thereof). The following can be given as examples of the anode material: an ITO (indium tin oxide); an IZO (indium zinc oxide), which is formed by mixing 2 to 20 atomic % zinc oxide (ZnO) into indium oxide containing silicon oxide; gold (Au); platinum (Pt); titanium (Ti); nickel (Ni); tungsten (W); chromium (Cr); molybdenum (Mo); iron (Fe); cobalt (Co); copper (Cu); palladium (Pd); a nitride of a metal material; and the like.

It is to be noted that the first buffer layer can be provided between the anode and the light-emitting layer, so that the first buffer layer makes an ohmic contact with various electrode materials. Therefore, a substance having a low work function can also be used as the anode material (e.g., aluminum (Al), silver (Ag), an alkali metal, an alkaline-earth metal, or an alloy thereof (such as Mg:Ag or Al:Li)).

The first buffer layer is formed of a metal compound and any one of an aromatic amine compound, a carbazole derivative, and aromatic hydrocarbon (including aromatic hydrocarbon having at least a vinyl skeleton).

In addition, a layer formed of the stilbene derivative of the present invention and a metal compound may be used as the first buffer layer.

As the aromatic amine compound, the following can be given as examples:
4,4'-bis[N-(1-naphthyl)-N-phenylamino]biphenyl (abbreviation: NPB); 4,4'-bis[N-(3-methylphenyl)-N-phenylamino]biphenyl (abbreviation.: TPD); 4,4',4''-tris(N,N-diphenylamino)triphenylamine (abbreviation.: TDATA); 4,4',4''-tris[N-(3-methylphenyl)-N-phenylamino]triphenylamine (abbreviation: MTDATA); N,N'-bis[4-[bis(3-methylphenyl)amino]phenyl]-N,N'-diphenyl-[1,1'-Biphenyl]-4,4'-diamine (abbreviation: DNTPD); 1,3,5-tris[N,N-di(m-tolyl)amino]benzene (abbreviation: m-MTDAB); 4,4',4''-tris(N-carbazolyl)triphenylamine (abbreviation: TCTA); 2,3-bis(4-diphenylaminophenyl)quinoxaline (abbreviation: TPAQn); 2,2',3,3'-tetrakis(4-diphenylaminophenyl)-6,6'-biquinoxaline (abbreviation: D-TriPhAQn); ,3-bis{4-[N-(1-naphthyl)-N-phenylamino]phenyl}-dibenzo[f,h]quinoxaline (abbreviation: NPADiBzQn); and the like.

As the carbazole derivative, the following can be given as examples: 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation.: PCzPCA2); N-(2-naphthyl)carbazole (abbreviation: NCz); 4,4'-di(N-carbazolyl)biphenyl (abbreviation: CBP); 9,10-bis[4-(N-carbazolyl)phenyl]anthracene (abbreviation: BCPA); 3,5-bis[4-(N-carbazolyl)phenyl]biphenyl (abbreviation.: BCPBi); 1,3,5-tris[4-(N-carbazolyl)phenyl]benzene (abbreviation: TCPB); and the like.

As the aromatic hydrocarbon, the following can be given as examples: anthracene, 9,10-diphenylanthracene (abbreviation: DPA); 2-tert-butyl-9,10-di(2-naphthyl)anthracene (abbreviation: t-BuDNA); tetracene; rubrene; pentacene; 4,4'-bis(2,2-diphenylvinyl)biphenyl (abbreviation: DPVBi); and the like.

As the above-described metal compound, an oxide or nitride of a transition metal is preferable, and an oxide or nitride of a metal which belongs to Group 4 to 8 is particularly preferable. In addition, a metal compound having a property that tends to accept an electron from the above-described aromatic amine, a carbazole derivative, and aromatic hydrocarbon (including aromatic hydrocarbon having at least a vinyl skeleton) is preferable. As the metal compound, for example, a molybdenum oxide, a vanadium oxide, a ruthenium oxide, a rhenium oxide, a titanium oxide, a chromium oxide, a zirconium oxide, a hafnium oxide, a tantalum oxide, a tungsten oxide, a silver oxide, and the like can be given.

It is to be noted that in the first buffer layer, the mass ratio of aromatic amine, a carbazole derivative, or aromatic hydrocarbon (including aromatic hydrocarbon having at least a vinyl skeleton) and a metal compound is preferably 0.5 to 2 (or the molar ratio is 1 to 4). In addition, the first buffer layer can be formed to have a thickness of greater than or equal to 50 nm because of its high conductivity. Forming the first buffer layer into a thickness of greater than or equal to 50 nm can prevent a short-circuit between the anode and the cathode.

As a cathode material, a substance having a low work function (work function of less than or equal to 3.8 eV) can be used (e.g., a metal, an alloy, a conductive compound, a mixture thereof, or the like). The following can be used as an example of the cathode material: an element belonging to Group 1 or 2 of the periodic table, that is, an alkali metal such as Li or Cs or an alkaline earth metal such as Mg, Ca, or Sr; an alloy (Mg:Ag, Al:Li) or a compound (LiF, CsF, or $CaF_2$)

containing the above element; a transition metal including a rare earth metal; Al; Ag; an ITO (indium tin oxide); and the like.

It is to be noted that the second buffer layer can be provided between the cathode and the light-emitting layer, so that the second buffer layer makes an ohmic contact with various electrode materials. Therefore, a substance having a high work function can be used as the cathode material (e.g., an ITO (indium tin oxide); an indium tin oxide containing silicon oxide; an IZO (indium zinc oxide), which is formed by mixing 2 to 20 atomic % zinc oxide (ZnO) into an indium oxide, containing silicon oxide; or the like).

The second buffer layer is formed of at least one substance selected from an electron transporting substance and a bipolar substance and a substance (donor) having a property that tends to release an electron to these materials. As the electron transporting substance or the bipolar substance, a substance having an electron mobility of greater than or equal to $1 \times 10^{-6}$ cm$^2$/Vs is preferable. Materials for each of the electron transporting substance and the bipolar substance will be described later.

It is to be noted that the anode material or the cathode material can be formed into a thin film by evaporation, sputtering, or the like. The thin film preferably has a thickness of 10 to 500 nm.

The structure of the light-emitting element of the present invention can be selected from a structure in which light generated from the layer 103 containing a light-emitting substance is emitted through only the anode; a structure in which light is emitted through only the cathode; and a structure in which light is emitted through both of the anode and cathode. In the case of employing the structure in which light is emitted through the anode, the anode is formed of a light-transmitting material. In the case of employing the structure in which light is emitted through the cathode, the cathode is formed of a light-transmitting material.

For the hole injecting layer, a porphyrin-based compound can be used when an organic compound is adopted. For example, phthalocyanine (hereinafter, referred to as H$_2$-Pc), copper phthalocyanine (hereinafter, referred to as Cu-Pc), or the like can be used. In addition, a chemically doped conductive high molecular compound can be used (e.g., polyethylene dioxythiophene (hereinafter, referred to as PEDOT) doped with polystyrene sulfonate (hereinafter, referred to as PSS)).

The hole transporting layer is preferably formed of a hole transporting substance or a bipolar substance having a hole mobility of greater than or equal to $1 \times 10^{-6}$ cm$^2$/Vs. The hole transporting substance refers to a substance having a hole mobility higher than an electron mobility.

As the hole transporting substance, for example, an aromatic amine-based compound (that is, a substance having a bond of benzene ring-nitrogen) can be used. For example, the following substances are widely used: 4,4'-bis[N-(3-methylphenyl)-N-phenylamino]biphenyl (hereinafter, referred to as TPD); 4,4'-bis[N-(1-naphthyl)-N-phenylamino]biphenyl (hereinafter, referred to as NPB), 4,4',4''-tris(N-carbazolyl)triphenylamine (hereinafter, referred to as TCTA); 4,4',4''-tris(N,N-diphenylamino)triphenylamine (hereinafter, referred to as TDATA); and 4,4',4''-tris[N-(3-methylphenyl)-N-phenylamino]triphenylamine (hereinafter, referred to as MTDATA).

The bipolar substance refers to a substance having a value of less than or equal to 100 which is obtained by dividing the higher of the hole mobility and the electron mobility by the lower. As the bipolar substance, for example, 2,3-bis(4-diphenylaminophenyl)quinoxaline (abbreviation.: TPAQn); 2,3-bis{4-[N-(1-naphthyl)-N-phenylamino]phenyl}-dibenzo[f,h]quinoxaline (abbreviation.: NPADiBzQn); and the like can be given. In particular, among the bipolar substances, a substance having both of a hole mobility and an electron mobility of greater than or equal to $1 \times 10^{-6}$ cm$^2$/Vs is preferable.

The light-emitting layer contains at least one kind of a light-emitting substance. The light-emitting substance refers to a substance that has excellent light-emitting efficiency and can emit light of a desired wavelength. It is to be noted that the light-emitting layer of this embodiment mode is formed using a stilbene derivative of the present invention as a host material.

By using a stilbene derivative of the present invention for a light-emitting layer, blue light emission can be obtained.

The electron transporting layer is preferably formed of an electron transporting substance or a bipolar substance having an electron mobility of greater than or equal to $1 \times 10^{-6}$ cm$^2$/Vs. It is to be noted that the electron transporting substance refers to a substance having an electron mobility higher than a hole mobility, and preferably a substance in which the ratio of an electron mobility to a hole mobility is greater than or equal to 100.

As the electron transporting substance, a metal complex having a quinoline skeleton such as tris(8-quinolinolato)aluminum (hereinafter, Alq$_3$), tris(4-methyl-8-quinolinolato)aluminum (hereinafter, Almq$_3$) or a benzoquinoline skeleton such as bis(10-hydroxybenzo[h]-quinolinato)beryllium (hereinafter, BeBq$_2$); a mixed ligand complex such as bis(2-methyl-8-quinolinolato)(4-phenylphenolate)aluminum (hereinafter, BAlq); or the like is preferable. In addition, a metal complex having an oxazole-based or thiazole-based ligand such as bis[2-(2-benzoxazolyl)phenolato]zinc (hereinafter, referred to as Zn(BOX)$_2$) or bis[2-(2'-hydroxyphenyl)-benzoxazolato]zinc (hereinafter, referred to as Zn(BTZ)$_2$) can be used. Furthermore, the following can be used as well as the metal complexes: an oxadiazole derivative such as 2-(4-biphenylyl)-5-(4-tert-butylphenyl)-1,3,4-oxadiazole (hereinafter, referred to as PBD) or 1,3-bis[5-(4-tert-butylphenyl)-1,3,4-oxadiazol-2-yl]benzene (hereinafter, referred to as OXD-7); a triazole derivative such as 3-(4-biphenylyl)-4-phenyl-5-(4-tert-butylphenyl)-1,2,4-triazole (hereinafter, referred to as TAZ) or 3-(4-tert-butylphenyl)-4-(4-ethylphenyl)-5-(4-biphenylyl)-1,2,4-triazole (hereinafter, referred to as p-EtTAZ); a phenanthroline derivative such as bathophenanthroline (hereinafter, referred to as BPhen) or bathocuproine (hereinafter, referred to as BCP); and, in addition, 4,4-bis(5-methylbenzoxazolyl-2-yl)stilbene (hereinafter, referred to as BzOs); and the like.

As the hole blocking substance, BAlq, OXD-7, TAZ, p-EtTAZ, BPhen, BCP, or the like can be used.

The light-emitting element is manufactured using the stilbene derivative of the present invention for the light-emitting layer in this manner; consequently, a blue light-emitting element can be obtained.

Embodiment Mode 4

A method for manufacturing a light-emitting device of the present invention will be described in this embodiment mode with reference to FIGS. 2A to 2E and FIGS. 3A to 3C. Although an example of manufacturing an active matrix light-emitting device will be illustrated in this embodiment mode, the present invention is also applicable to a passive matrix light-emitting device as described in Embodiment Mode 6.

First, a first base insulating layer 51a and a second base insulating layer 51b are formed over a first substrate 50. Thereafter, a semiconductor layer is formed over the second base insulating layer 51b.

As a material for the first substrate 50, glass, quartz, plastic (e.g., polyimide, an acrylic resin, polyethyleneterephthalate, polycarbonate, polyacrylate, polyethersulfone, or the like), or the like can be used. The first substrate 50 of such a material can be polished by CMP or the like before use, if required. In this embodiment mode, glass is used.

The first base insulating layer 51a and the second base insulating layer 51b are provided in order to prevent an element such as an alkali metal or an alkaline earth metal, which is contained in the first substrate 50 and adversely affects a characteristic of the semiconductor layer, from dispersing in the semiconductor layer. As materials of the first and second base insulating layers, a silicon oxide, a silicon nitride, a silicon oxide containing nitrogen, a silicon nitride containing oxygen, or the like can be used. In this embodiment mode, the first base insulating layer 51a and the second base insulating layer 51b are formed of a silicon nitride and a silicon oxide, respectively. A two-layer structure of the first base insulating layer 51a and the second base insulating layer 51b is employed in this embodiment mode. Alternatively, a base insulating layer may be provided as a single-layer structure or a stacked-layer structure of three or more layers.

Next, the semiconductor layer is formed. A silicon film is employed in this embodiment mode. An amorphous silicon film is formed over the second base insulating layer 51b so as to have a thickness of 25 to 100 nm (preferably, 30 to 60 nm). As a method for forming the amorphous silicon film, a known method such as a sputtering method, a low-pressure CVD method, or a plasma CVD method can be used. Thereafter, the amorphous silicon film is subjected to heat treatment at 500° C. for 1 hour, and thus the amorphous silicon film is dehydrogenated.

Subsequently, the amorphous silicon film is formed into a crystalline silicon film by laser crystallization. In this embodiment mode, an excimer laser is used in the laser crystallization.

Other methods may be employed for crystallizing the amorphous silicon film. For example, there are a method by which crystallization is performed only by heat treatment, a method by which crystallization is performed by heat treatment with the use of a catalytic element promoting crystallization, and the like. As the element promoting crystallization, nickel, iron, palladium, tin, lead, cobalt, platinum, copper, gold, or the like can be given. In a method by which crystallization is performed by heat treatment with the use of a catalytic element promoting crystallization, crystallization at a lower temperature in a shorter time is possible as compared with a method by which crystallization is performed only by heat treatment.

Next, a minute amount of an impurity to control a threshold value is added to the semiconductor layer, if required (so-called channel doping). For adding an impurity, an impurity imparting N-type conductivity (such as phosphorus) or P-type conductivity (such as boron) is used and an ion doping method or the like is employed.

Thereafter, the semiconductor layer is patterned into a predetermined shape as follows. A photoresist is formed over the semiconductor layer, the photoresist is exposed to light to form a predetermined mask shape, and then the photoresist is baked to form a resist mask over the semiconductor layer; then the semiconductor layer is etched using the resist mask as a mask. Thus, the island-like semiconductor layer 52 can be formed.

Next, a gate insulating layer 53 is formed so as to cover the island-like semiconductor layer 52. The gate insulating layer 53 is formed by a plasma CVD method or a sputtering method. In this embodiment mode, the gate insulating layer 53 is formed of a silicon oxide. The gate insulating layer 53 is formed so as to have a film thickness of 40 to 150 nm.

Subsequently, a gate electrode 54 is formed over the gate insulating layer 53. The gate electrode 54 can be formed of an element selected from tantalum, tungsten, titanium, molybdenum, aluminum, copper, chromium, and niobium; or an alloy material or a compound material mainly containing the above element. Alternatively, a polycrystalline silicon film doped with an impurity element such as phosphorus may be used. In addition, an AgPdCu alloy may be used.

In this embodiment mode, the gate electrode 54 is formed as a single-layer structure. Alternatively, the gate electrode 54 may have a stacked-layer structure. For example, a stacked-layer structure including a lower layer formed of tungsten and an upper layer formed of molybdenum is given.

Next, an impurity is added at high concentration to the island-like semiconductor layer 52 using the gate electrode 54 as a mask. Accordingly, a thin film transistor 70 having the island-like semiconductor layer 52, the gate insulating layer 53, and the gate electrode 54 is formed.

It is to be noted that a manufacturing process of a thin film transistor is not particularly limited and may be appropriately changed so that a transistor having a desired structure can be manufactured.

In this embodiment mode, a top-gate thin film transistor formed using the crystalline silicon film crystallized by laser crystallization is used. Alternatively, a bottom-gate thin film transistor can be used for a pixel portion.

Adding an impurity element will be explained. The impurity element refers to an element that can impart one conductivity type to the island-like semiconductor layer 52. As an impurity element imparting N-type conductivity, phosphorus can be given. As an impurity element imparting P-type conductivity, boron or the like can be given. When the first electrode 101 of the light-emitting element serves as an anode, selecting the impurity element imparting P-type conductivity is desirable. On the other hand, when the first electrode 101 of the light-emitting element serves as a cathode, selecting the impurity element imparting N-type conductivity is desirable.

Figure 2A:
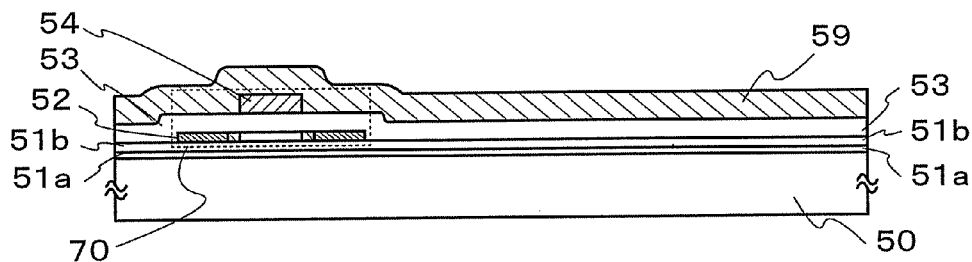
FIGS. 2A to 2E are cross-sectional views illustrating a manufacturing method for an active matrix light-emitting device of the present invention.

Thereafter, an insulating film 59 is formed of a silicon nitride so as to cover the gate insulating layer 53 and the gate electrode 54. After the insulating film 59 is formed, heat treatment is performed at 480° C. for approximately 1 hour, and thus the impurity element is activated and the island-like semiconductor layer 52 is hydrogenated. (FIG. 2A)

Figure 2B:
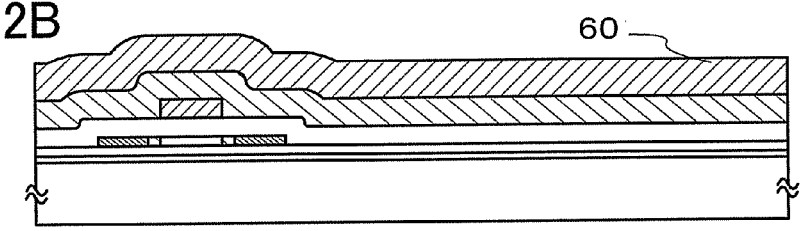

Next, a first interlayer insulating layer 60 to cover the insulating film 59 is formed. As a material for the first interlayer insulating layer 60, a silicon oxide, an acrylic resin, polyimide, siloxane, or the like is preferable. In this embodiment mode, a silicon oxide film is used to form the first interlayer insulating layer 60. (FIG. 2B)

Figure 2C:
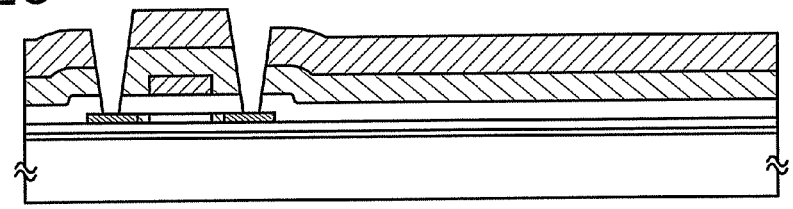

Next, contact holes to reach the island-like semiconductor layer 52 are formed. The contact holes can be formed using a resist mask by etching until the island-like semiconductor layer 52 is exposed. (FIG. 2C)

Figure 2D:
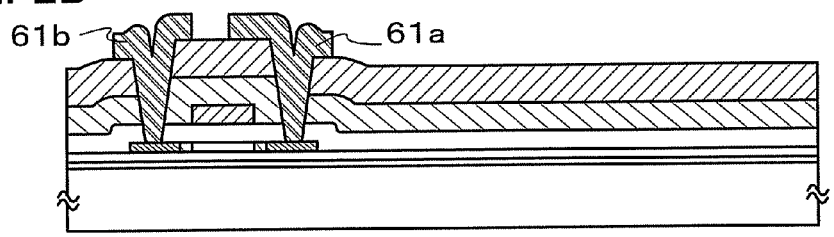

Thereafter, a conductive layer is formed. This conductive layer is processed into a desired shape and a connection portion 61a, a first wiring 61b, and the like are formed. This wiring is formed as a single-layer structure or a stacked-layer structure of aluminum, copper, an aluminum-carbon-nickel alloy, an aluminum-carbon-molybdenum alloy, or the like. (FIG. 2D)

Figure 2E:
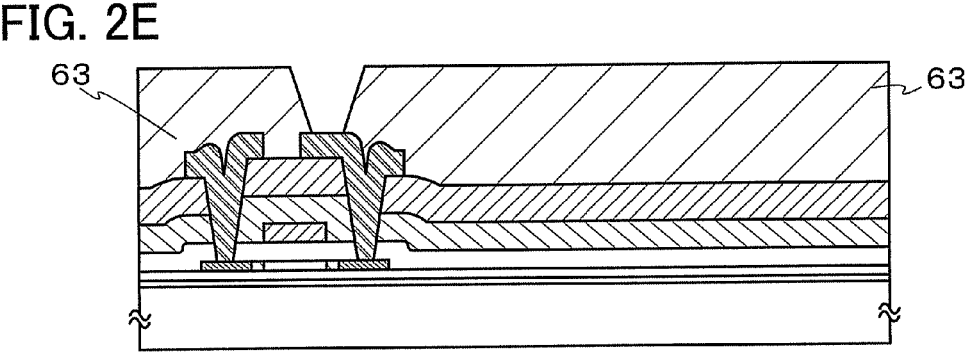

Thereafter, a second interlayer insulating layer 63 is formed. As a material for the second interlayer insulating layer 63, an acrylic resin, polyimide, siloxane, or the like can be used. In this embodiment mode, siloxane is used as the material for the second interlayer insulating layer 63. (FIG. 2E)

Next, an inorganic insulating layer may be formed of a silicon nitride or the like over the second interlayer insulating layer 63. Providing the inorganic insulating layer can prevent the second interlayer insulating layer 63 from being etched more than necessary in a later step of etching a pixel electrode. Next, a contact hole to reach the connection portion 61a through the second interlayer insulating layer 63 is formed.

Subsequently, a conductive layer having a light transmitting property is formed. Thereafter, the conductive layer having a light transmitting property is processed and a lower electrode 64 is formed. The lower electrode 64 is in contact with the connection portion 61a.

As a material for the lower electrode 64, the following material can be used: a conductive metal such as aluminum (Al), silver (Ag), gold (Au), platinum (Pt), nickel (Ni), tungsten (W), chromium (Cr), molybdenum (Mo), iron (Fe), cobalt (Co), copper (Cu), palladium (Pd), lithium (Li), cesium (Cs), magnesium (Mg), calcium (Ca), strontium (Sr), or titanium (Ti); an alloy such as an aluminum-silicon (Al—Si) alloy, an aluminum-titanium (Al—Ti) alloy, or an aluminum-silicon-copper (Al—Si—Cu) alloy; a nitride of a metal material such as a titanium nitride; a metal compound such as an indium tin oxide (ITO), an ITO containing silicon, or an indium zinc oxide (IZO) formed by mixing a 2 to 20% zinc oxide (ZnO) into an indium oxide; or the like.

Figure 3A:
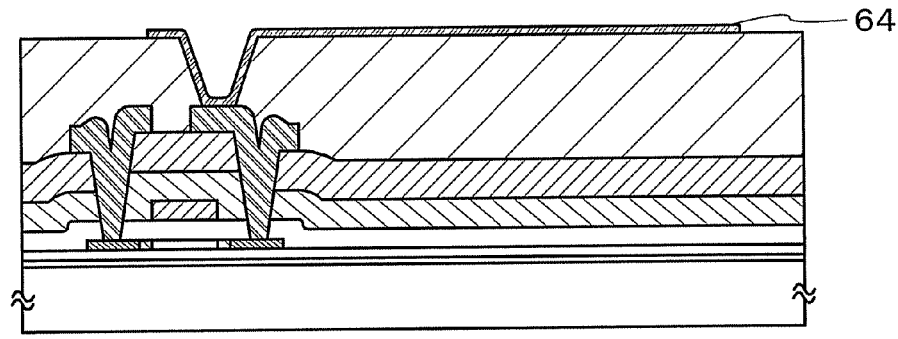
FIGS. 3A to 3C are cross-sectional views illustrating a manufacturing method for an active matrix light-emitting device of the present invention.

Further, the electrode through which light is extracted is formed of a conductive film having a light transmitting property. As a material for the conductive film having a light transmitting property, a thin film of a metal such as Al or Ag is used, as well as a metal compound such as an ITO (indium tin oxide), an ITO containing silicon (hereinafter also referred to as an ITSO), or an IZO (indium zinc oxide) formed by mixing a 2 to 20% oxide (ZnO) into an indium oxide. In the case where light is extracted from the second electrode 102, the lower electrode 64 can be formed of a material having high reflectivity (such as Al or Ag). In this embodiment mode, an ITSO is used as the material for the lower electrode 64. (FIG. 3A)

Figure 3B:
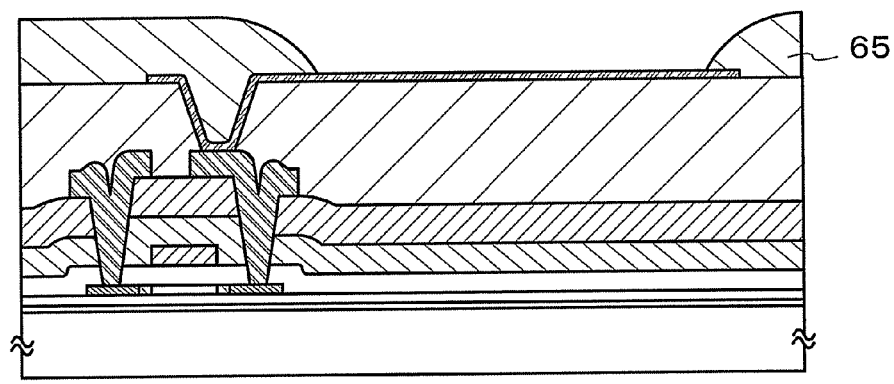
Figure 3C:
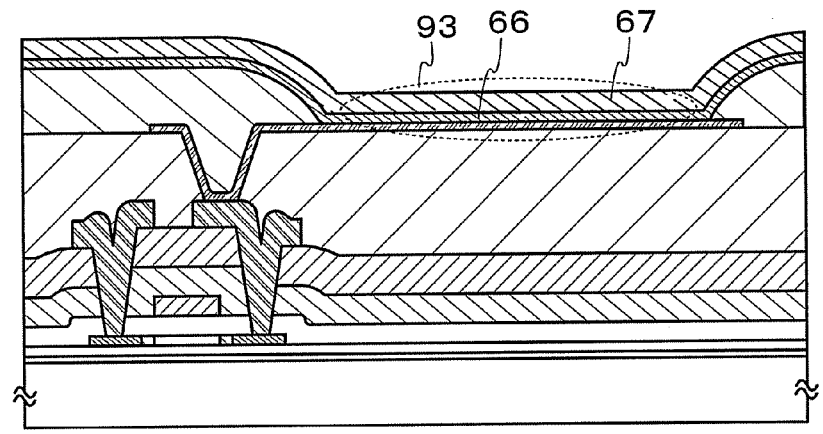

Next, an insulating layer is formed of an organic material or an inorganic material. Subsequently, the insulating layer is processed so as to expose part of the lower electrode 64, and thus a partition wall 65 is formed. A photosensitive organic material (such as an acrylic resin or polyimide) can be used as a material for the partition wall 65. It is to be noted that a nonphotosensitive organic or inorganic material may be used as the material for the partition wall 65. (FIG. 3B)

Next, a layer containing a light-emitting substance 66 is formed. Subsequently, an upper electrode 67 to cover the layer containing a light-emitting substance 66 is formed. Accordingly, a light-emitting element portion 93 including the layer containing a light-emitting substance 66 interposed between the lower electrode 64 and the upper electrode 67 can be manufactured. Then, light emission can be obtained by applying voltage to the light-emitting element portion. As a material for the upper electrode 67, a similar material as the lower electrode 64 can be used. In this embodiment mode, aluminum is used as the material for the upper electrode 67.

The layer containing a light-emitting substance 66 is formed by an evaporation method, an ink-jet method, a spin coating method, a dip coating method, or the like. The layer containing a light-emitting substance 66 contains a stilbene derivative of the present application. The layer containing a light-emitting substance 66 may be a stacked layer of layers having various functions as described in Embodiment Mode 3 or a single layer of a light-emitting layer. Further, the material described in Embodiment Mode 1 is contained as a light-emitting layer in the layer containing a light-emitting substance 66. The material described in Embodiment Mode 1 may be contained as a host or a dopant of the light-emitting layer. In addition, the material described in Embodiment Mode 1 may be contained in a layer other than the light-emitting layer or part thereof in the layer containing a light-emitting substance. Further, a material used in combination with the material described in Embodiment Mode 1 may be a low molecular material, an intermediate molecular material (including oligomer and dendrimer), or a high molecular material. Further, as a material used for the layer containing a light-emitting substance 66, a single layer or a stacked layer of an organic compound is generally employed. In the present invention, however, the layer containing a light-emitting substance 66 may also be formed as a structure in which an inorganic compound is used for part of a film formed of an organic compound.

Thereafter, a silicon oxide film containing nitrogen is formed as a passivation film by a plasma CVD method. A silicon oxynitride film may be formed by a plasma CVD method using $SiH_4$, $N_2O$, and $NH_3$; using $SiH_4$ and $N_2O$; or using a gas in which $SiH_4$ and $N_2O$ are diluted with Ar.

Alternatively, a silicon oxynitride film formed using $SiH_4$, $N_2O$, and $H_2$ may be employed as the passivation film.

Subsequently, a display portion is sealed in order to protect the light-emitting element from a substance (such as moisture) promoting deterioration of the light-emitting element. In the case of using a second substrate 94 for the sealing, it is attached with the use of a sealing material having an insulating property so that an external connection portion is exposed. Next, a flexible wiring board is attached to the external connection portion; accordingly, a light-emitting device is completed.

An example of a structure of the light-emitting device manufactured as described above will be explained with reference to FIGS. 4A and 4B. It is to be noted that portions having similar functions are denoted by the same reference numerals even if they have different shapes, and the explanation thereof may be omitted. In this embodiment mode, the thin film transistor 70 having an LDD structure is connected to the light-emitting element portion 93 through the connection portion 61a.

Figure 4A:
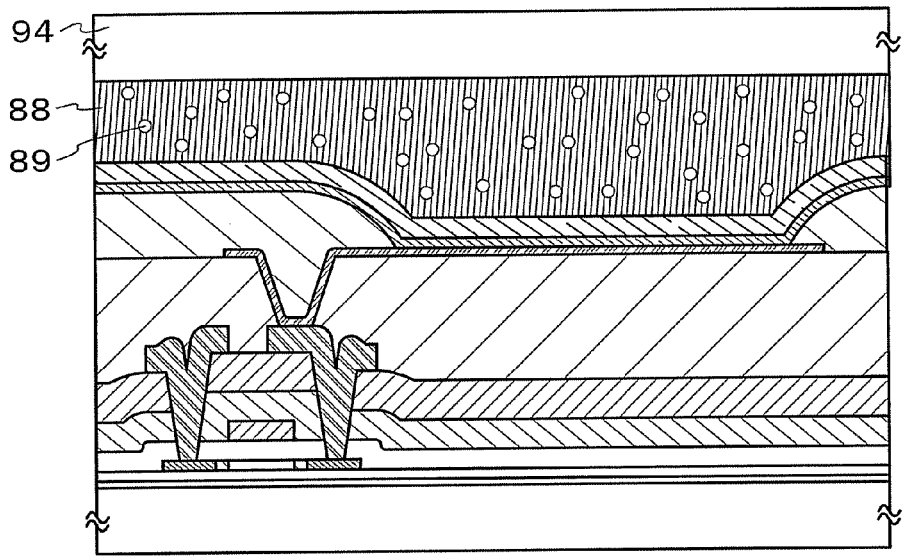
FIGS. 4A and 4B are cross-sectional views of a light-emitting device of the present invention.

FIG. 4A illustrates a structure where the lower electrode 64 is formed of a conductive film having a light transmitting property and light is emitted through the first substrate 50. It is to be noted that, after the light-emitting element portion 93 is formed, the second substrate 94 is firmly attached to the first substrate 50 with the use of a sealing material or the like. A space between the second substrate 94 and the element is filled with a resin 88 having a light transmitting property or the like to seal the light-emitting element portion. Accordingly, the deterioration due to moisture of the light-emitting element portion 93 can be prevented. It is desirable that the resin 88 having a light transmitting property have a hygroscopic property. Further, a drying agent 89 having a higher light transmitting property is desirably dispersed in the resin 88 having a light transmitting property; thus, an adverse effect of moisture can be prevented.

Figure 4B:
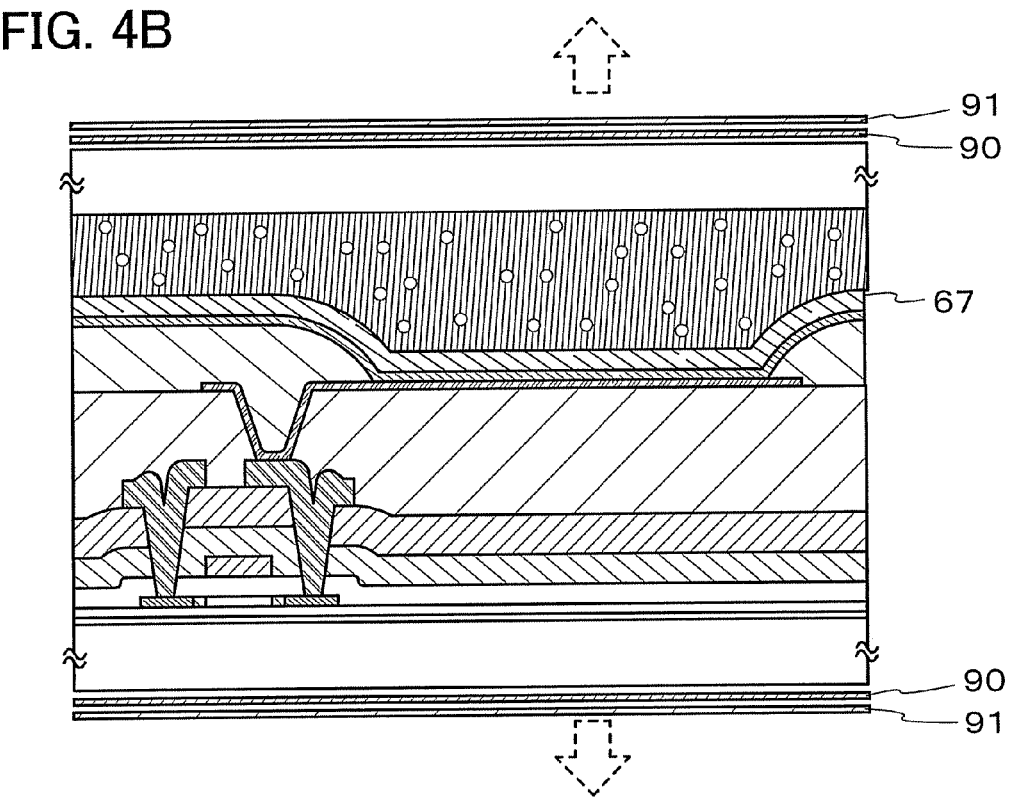

FIG. 4B illustrates a structure where both of the lower electrode 64 and the upper electrode 67 are formed of conductive films each having a light transmitting property and light can be emitted through both of the first substrate 50 and the second substrate 94. In this structure, a screen can be prevented from being transparent with outer polarizing plates 90 provided outside of the first substrate 50 and the second substrate 94; therefore, visibility is improved. Protection films 91 are preferably provided outside of the outer polarizing plates 90.

It is to be noted that either analog video signals or digital video signals may be employed as signals supplied to the light-emitting device having a display function of the present invention.

This embodiment mode can be combined with any of the other embodiment modes.

Embodiment Mode 5

Figure 5A:
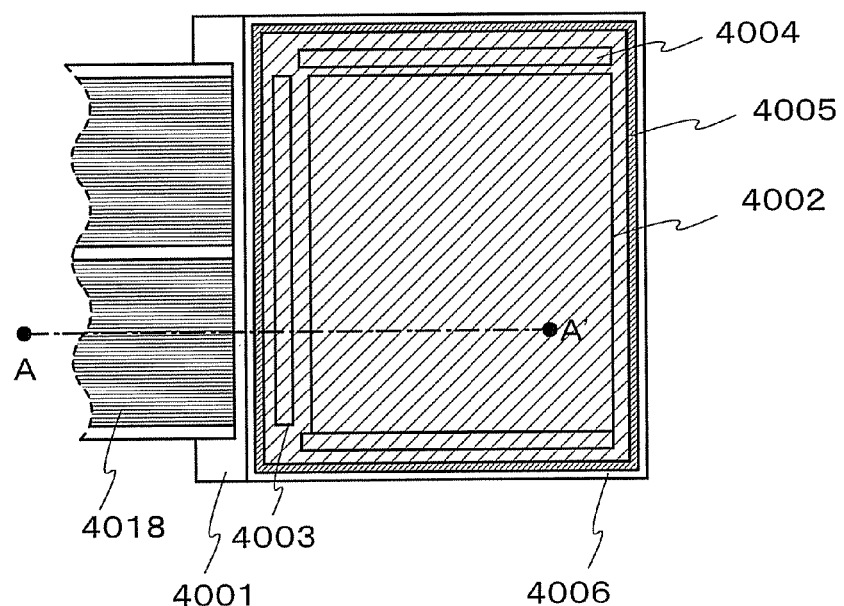
FIGS. 5A and 5B are a top view and a cross-sectional view, respectively, of a light-emitting device of the present invention.
Figure 5B:
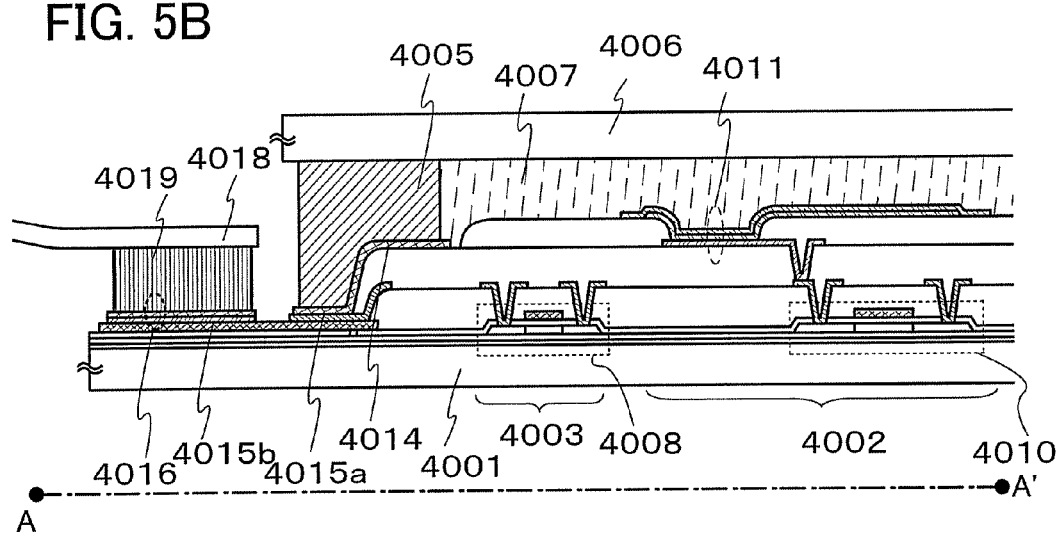

In this embodiment mode, the appearance of a panel that is a light-emitting device of the present invention will be described with reference to FIGS. 5A and 5B. FIG. 5A is a top view of the panel, in which a transistor and a light-emitting element are sealed by a TFT substrate 4001, an opposing substrate 4006, and a sealing material 4005. FIG. 5B corresponds to a cross-sectional view of FIG. 5A. Each of the light-emitting elements described in the other embodiment modes are applicable to a light-emitting element mounted to this panel.

The sealing material 4005 is provided so as to surround a pixel region 4002, a signal line driver circuit 4003, and a scan line driver circuit 4004 which are provided over the TFT substrate 4001. The opposing substrate 4006 is provided over the pixel region 4002, the signal line driver circuit 4003, and the scan line driver circuit 4004. Further, a filler 4007 is tightly sealed together with the pixel region 4002, the signal line driver circuit 4003, and the scan line driver circuit 4004.

The pixel region 4002, the signal line driver circuit 4003, and the scan line driver circuit 4004 each include a plurality of thin film transistors. FIG. 5B illustrates a driver-circuit-portion thin film transistor 4008 included in the signal line driver circuit 4003 and a pixel-portion thin film transistor 4010 included in the pixel region 4002.

A light-emitting element portion 4011 is electrically connected to the pixel-portion thin film transistor 4010.

A first lead wiring 4014 corresponds to a wiring to supply signals or power supply voltage to the pixel region 4002, the signal line driver circuit 4003, and the scan line driver circuit 4004. The first lead wiring 4014 is connected to a connection terminal 4016 through a second lead wiring 4015a and a third lead wiring 4015b. The connection terminal 4016 is electrically connected to a terminal included in a flexible printed circuit (hereinafter, referred to as an FPC 4018) through an anisotropic conductive film 4019.

It is to be noted that an ultraviolet curing resin or a thermosetting resin as well as an inert gas such as nitrogen or argon can be used as the filler 4007. For example, polyvinyl chloride, an acrylic resin, polyimide, an epoxy resin, a silicon resin, polyvinyl butyral, or the like can be used.

It is to be noted that the light-emitting device of the present invention includes, in its category, a panel provided with a pixel portion including a light-emitting element and a module in which an IC is mounted to the panel.

This embodiment mode can be combined with any of the other embodiment modes.

Embodiment Mode 6

Figure 6A:
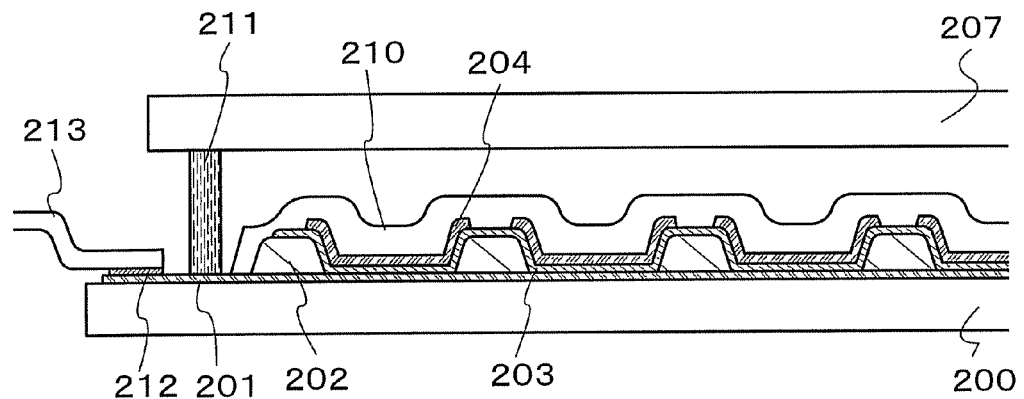
FIGS. 6A and 6B are a cross-sectional view and a top view, respectively, of a light-emitting device of the present invention.

An example of a structure of a light-emitting device of the present invention is illustrated in FIG. 6A. FIG. 6A is a cross-sectional view illustrating a pixel portion of a passive matrix light-emitting device. The light-emitting device of the present invention illustrated in FIG. 6A has a first substrate 200, first electrodes 201 of light-emitting elements, a partition wall 202, a layer 203 containing a light-emitting substance, second electrodes 204 of the light-emitting elements, and a second substrate 207.

A portion to serve as a pixel is a portion where the layer 203 containing a light-emitting substance is interposed between the first electrode 201 and the second electrode 204. The first electrodes 201 and the second electrodes 204 are formed in a striped pattern so as to be perpendicular to each other, and portions to serve as pixels are formed at the intersections. The partition wall 202 is formed parallel to the second electrodes 204. The portion to serve as a pixel is insulated by the partition wall 202 from another portion to serve as a pixel having the same first electrode 201.

In this embodiment mode, Embodiment Mode 5 may be referred to for specific materials and structures of the first electrodes 201, the second electrodes 204, and the layer 203 containing a light-emitting substance.

In addition, the first substrate 200, the partition wall 202, and the second substrate 207 in FIG. 6A correspond to the first substrate 50, the partition wall 65, and the second substrate 94 in Embodiment Mode 4, respectively. Structures, materials, and effects thereof are the same as those in Embodiment Mode 5; therefore, the explanation will not be repeated. Refer to the description in Embodiment Mode 5.

In the light emitting device, a protective film 210 is formed in order to prevent the entry of moisture or the like. The second substrate 207 formed of glass, quartz, a ceramic material such as alumina, a synthetic material, or the like is firmly attached with the use of a sealing adhesive 211. An external input terminal portion is connected to an external circuit with the use of a flexible printed wiring board 213 with an anisotropic conductive film 212 interposed therebetween. The protective film 210 can be formed of a silicon nitride or the like.

Figure 6B:
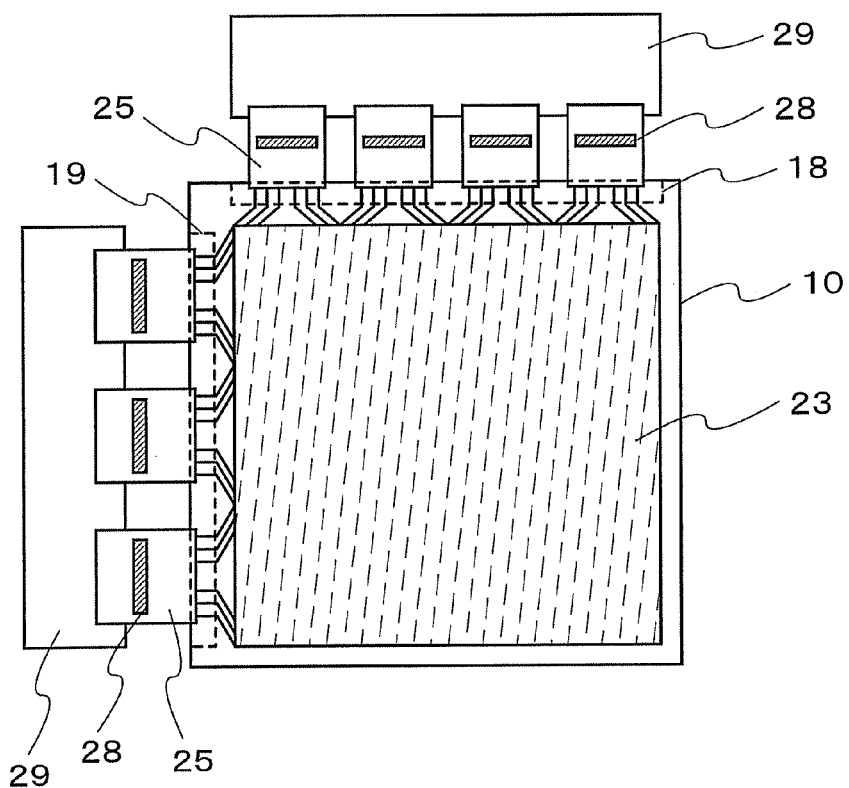

FIG. 6B illustrates a state of a module formed by connecting the external circuit to the panel illustrated in FIG. 6A. A flexible printed wiring board 25 is firmly attached to external input terminal portions 18 and 19; thus, the module is electrically connected to external circuit boards which are each provided with a power supply circuit and a signal processing circuit. A driver IC 28 which is one of external circuits may be mounted by either a COG method or a TAB method. FIG. 6B illustrates a state in which the driver IC 28 which is one of external circuits is mounted by a COG method. The signal processing circuit formed over the external circuit board and the driver IC 28 serves as a control circuit of the light-emitting element. Lighting and non-lighting or luminance of the light-emitting element is controlled by the control circuit; therefore a light-emitting device and an electronic appliance provided with the control circuit can display various images on the panel.

It is to be noted that the panel and the module correspond to one mode of a light-emitting device of the present invention and are both included in the scope of the present invention.

Embodiment Mode 7

As electronic appliances provided with a light-emitting device (module) of the present invention, the following applications are given: a video camera, a digital camera, a goggle type display (head-mounted display), a navigation system, a sound reproduction device (such as a car audio component), a computer, a game machine, a portable information terminal (such as a mobile computer, a mobile phone, a portable game machine, or an electronic book), an image reproduction device equipped with a recording medium (specifically, a device which reproduces a recording medium such as a digital versatile disc (DVD) and is equipped with a display to display the image), and the like. Examples of the above electronic appliances are illustrated in FIGS. 7A to 7E.

Figure 7A:
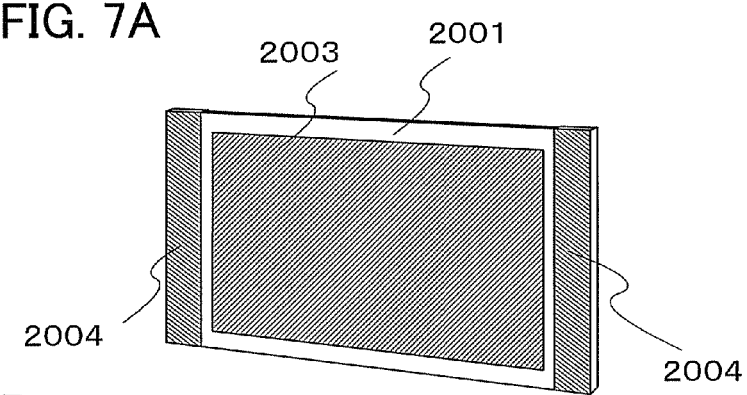
FIGS. 7A to 7E are views of examples of electronic appliances to which the present invention can be applied.

FIG. 7A illustrates a light-emitting device corresponding to a TV receiver, a monitor of a personal computer, or the like. The light-emitting device includes a chassis 2001, a display portion 2003, a speaker portion 2004, and the like. The light-emitting device of the present invention is a highly reliable light-emitting device, of which the display portion 2003 has a high display quality. A polarizing plate or a circularly polarizing plate is preferably provided in the pixel portion in order to enhance contrast.

Figure 7B:
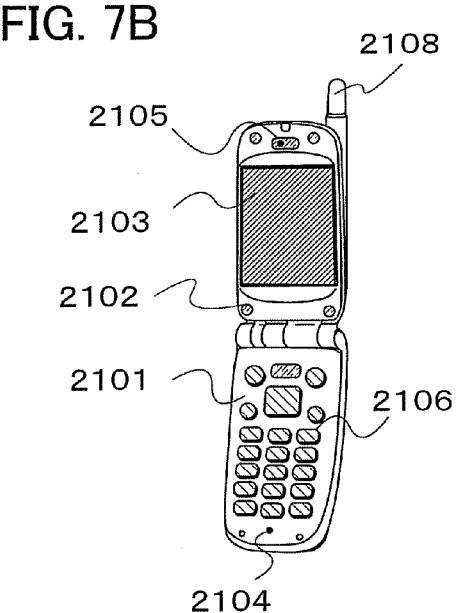

FIG. 7B illustrates a mobile phone, which includes a main body 2101, a chassis 2102, a display portion 2103, an audio input portion 2104, an audio output portion 2105, an operation key 2106, an antenna 2108, and the like. The mobile phone of the present invention is a highly reliable mobile phone, of which the display portion 2103 has a high display quality.

Figure 7C:
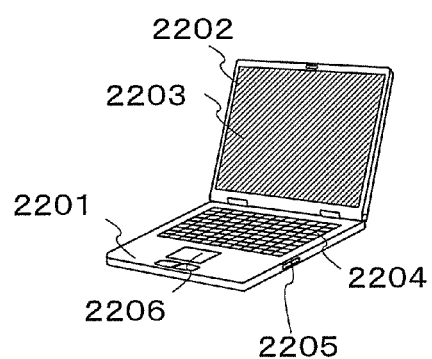

FIG. 7C illustrates a computer, which includes a main body 2201, a chassis 2202, a display portion 2203, a keyboard 2204, an external connection port 2205, a pointing device 2206, and the like. The computer of the present invention is a highly reliable computer, of which the display portion 2203 has a high display quality. Although a notebook computer is illustrated in FIG. 7C as an example, the present invention can be also applied to a desktop computer provided with a combined hard disk and display portion and the like.

Figure 7D:
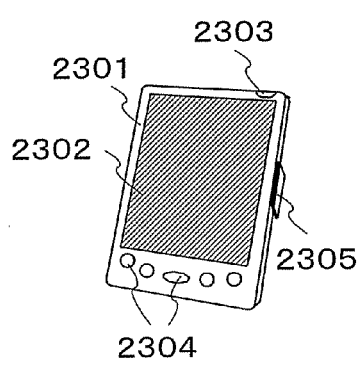

FIG. 7D illustrates a mobile computer, which includes a main body 2301, a display portion 2302, a switch 2303, an operation key 2304, an infrared port 2305, and the like. The mobile computer of the present invention is a highly reliable mobile computer, of which the display portion 2302 has a high display quality.

Figure 7E:
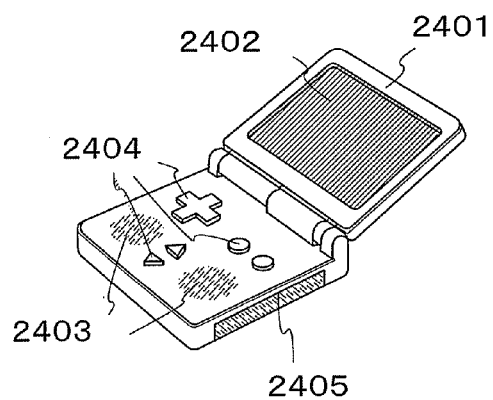

FIG. 7E illustrates a portable game machine which includes a chassis 2401, a display portion 2402, a speaker portion 2403, an operation key 2404, a recording medium insertion portion 2405, and the like. The portable game machine of the present invention is a highly reliable portable game machine, of which the display portion 2402 has a high display quality.

As described above, an applicable range of the present invention is extremely wide; therefore, the present invention can be applied to electronic appliances of various fields.

Embodiment 1

A synthetic method of (E)-4,4'-bis[4-(10-phenyl-9-anthryl)phenyl]stilbene (hereinafter, referred to as PAP2S), which is a compound represented by structural formula (16) of Embodiment Mode 1 as an example of an anthracene derivative of the present invention, will be described.

Step 1: Synthesis of (E)-4,4'-dibromostilbene (i) Synthesis of 4-bromobenzyltriphenylphosphonium bromide 25.2 g (101 mmol) of 4-bromobenzylbromide and 100 mL of acetone were put into a 200 mL conical flask, and then 29.1 g (111 mmol) of triphenylphosphine was added thereto. Thereafter, this mixture was stirred at room temperature for 23 hours to be reacted. After the reaction, a precipitate in the reaction mixture was collected by suction filtration. Then, 50.5 g of objective 4-bromobenzyltriphenylphosphonium bromide was obtained as a white powdered solid in a yield of 98%. Synthetic scheme of 4-bromobenzyltriphenylphosphonium bromide is illustrated below (synthetic scheme a-1).

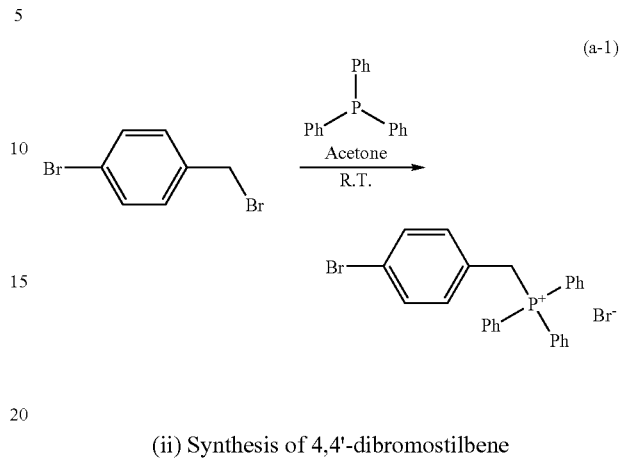

(ii) Synthesis of 4,4'-dibromostilbene 50.2 g (97.9 mmol) of 4-bromobenzyltriphenylphosphonium bromide and 21.7 g (118 mmol) of 4-bromobenzaldehyde were put into a 500 mL three-necked flask. Then, the atmosphere in the flask was substituted with nitrogen. Thereafter, 200 mL of tetrahydrofuran (abbreviation: THF) was added to the mixture. A suspension obtained by mixing 13.2 g (118 mmol) of potassium-tert-butoxide into 100 mL of THF was dropped to this mixture. Thereafter, the mixture was stirred at room temperature for 24 hours to be reacted. After the reaction, the reaction solution was washed with water, and then a precipitate was collected by suction filtration. Then, 14.0 g of objective (E)-4,4'-dibromostilbene was obtained as a white powdered solid in a yield of 42%. Further, the filtrate from which the precipitate was collected was extracted with ethylacetate and the extracted solution was dried over magnesium sulfate. After the drying, the mixture was subjected to suction filtration and the filtrate was condensed. The obtained residue was purified by silica gel column chromatography (developing solution: toluene). The obtained solution was condensed; then 14.8 g of (Z)-4,4'-dibromostilbene was obtained as a light yellow solid in a yield of 45%. Synthetic scheme of 4,4'-dibromostilbene is illustrated below (synthetic scheme a-2).

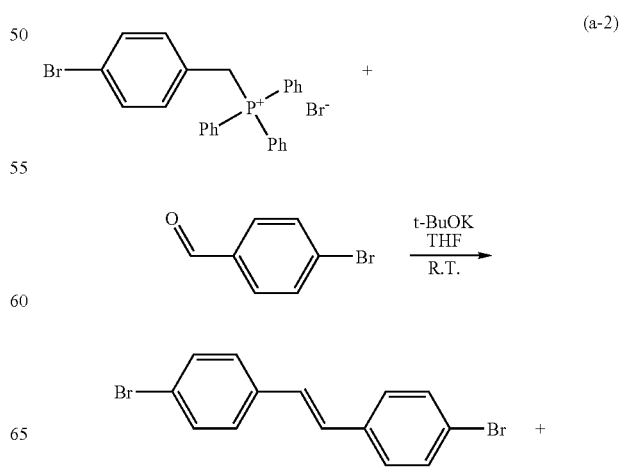

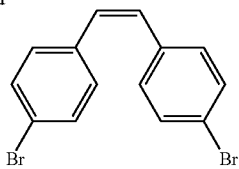

Step 2: Synthesis of 4-(10-phenyl-9-anthryl)phenylboronic acid (i) Synthesis of 9-phenylanthracene 25.4 g (100 mmol) of 9-bromoanthracene, 12.8 g (105 mmol) of phenylboronic acid, 0.233 g (1.00 mmol) of palladium (II) acetate, and 0.913 g (3.00 mmol) of tri(ortho-tolyl)phosphine were put into a 500 mL three-necked flask. Then, the atmosphere in the flask was substituted with nitrogen. Thereafter, 100 mL of ethylene glycol dimethyl ether (abbreviation: DME) and 75 mL (150 mmol) of potassium carbonate solution (2.0 mol/L) were added to the mixture, and this mixture was refluxed at 90° C. for 6 hours to be reacted. After the reaction, a precipitate in the reaction mixture was collected by suction filtration. The obtained solid was recrystallized by a mixed solvent of chloroform and hexane; then 20.8 g of objective 9-phenylanthracene was obtained as a white powdered solid in a yield of 82%. A synthetic scheme of 9-phenylanthracene is illustrated below (synthetic scheme b-1).

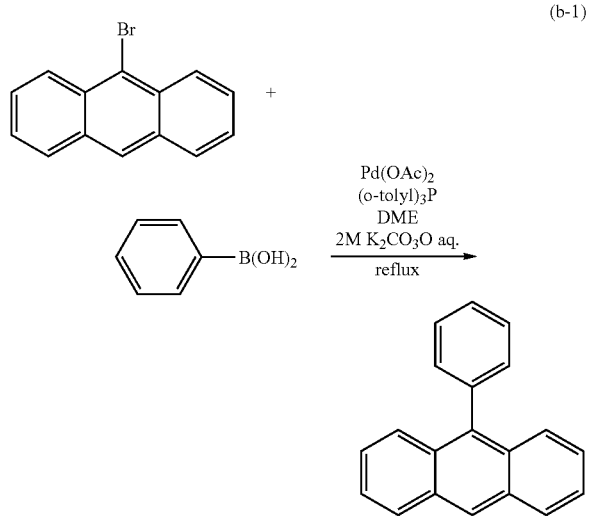

(b-1)

(ii) Synthesis method of 9-bromo-10-phenylanthracene 20.8 g (81.7 mmol) of 9-phenylanthracene and 300 mL of carbon tetrachloride were put into a 500 mL three-necked flask. A solution obtained by dissolving 13.1 g (81.7 mmol) of bromine in 5.00 mL of carbon tetrachloride was dropped into the mixture. After the dropping was completed, the reaction solution was stirred at room temperature for 3 hours to be reacted. Then, about 100 mL of a sodium thiosulfate solution was added to the reaction solution to complete the reaction. An organic layer of the mixture was washed with water and dried over magnesium sulfate. After the drying, the mixture was subjected to suction filtration, and the filtrate was condensed to obtain a solid. The obtained solid was recrystallized by a mixed solvent of chloroform and hexane; then 23.8 g of objective 9-bromo-10-phenylanthracene was obtained as a light yellow powdered solid in a yield of 71%. A synthetic scheme of 9-bromo-10-phenylanthracene is illustrated below (synthetic scheme b-2).

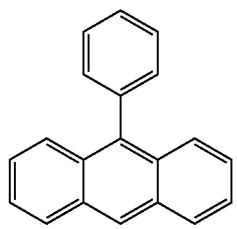
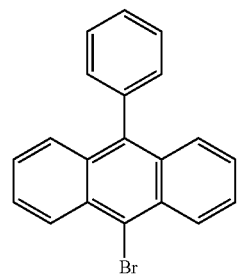

(b-2)

(iii) Synthesis method of 9-iodine-10-phenylanthracene 10 g (30 mmol) of 9-bromo-10-phenylanthracene was put into a 500 mL three-necked flask. Then, the atmosphere in the flask was substituted with nitrogen. 200 mL of tetrahydrofuran (abbreviation: THF) was added thereto. Thereafter, the flask was put into a constant low temperature bath and the reaction solution was cooled to −40° C. After 36 mL (23 mmol) of n-butyllithium (1.54 mol/L hexane solution) was dropped into this solution, the solution was stirred at −40° C. for 1 hour to be reacted. After the solution was stirred, a solution obtained by dissolving 9.1 g (39 mmol) of iodine in 40 mL of THF was dropped into the reaction solution for 1 hour with the temperature kept at −40° C. Then, the reaction solution was stirred for 1 hour with the temperature kept at −40° C. Thereafter, the flask Was taken out from the constant low temperature bath and the reaction solution was stirred for 24 hours to be returned to room temperature. Thereafter, about 100 mL of an aqueous sodium thiosulfate solution was added to the reaction solution to complete the reaction. An organic layer of the mixture was washed with water and a saturated aqueous sodium chloride solution, and dried over magnesium sulfate. After the drying, the mixture was subjected to suction filtration, and the filtrate was condensed to obtain a residue. The obtained residue was dissolved in toluene and subjected to suction filtration through Florisil, celite, and then alumina. The filtrate was condensed; then 29 g of objective 9-iodine-10-phenylanthracene was obtained as a yellow solid in a yield of 96%. A synthetic scheme of 9-iodine-10-phenylanthracene is illustrated below (synthetic scheme b-3).

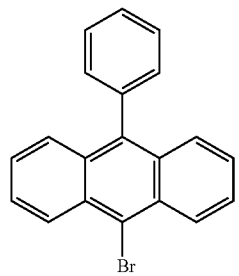

1) n-BuLi, THF, -40° C.
2) I₂, THF
   -40° C. → R.T.

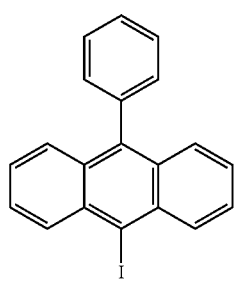

(iv) Synthesis method of
9-(4-bromophenyl)-10-phenylanthracene 5.3 g (14 mmol) of 9-iodine-10-phenylanthracene, 2.9 g (14 mmol) of 4-bromophenyl boronic acid, and 0.18 g (0.15 mmol) of tetrakis(triphenylphosphine)palladium(0) were put into a 100 mL three-necked flask. Then, the atmosphere in the flask was substituted with nitrogen. 30 mL of toluene and 15 mL (31 mmol) of an aqueous sodium carbonate solution (2.0 mol/L) were added to the mixture. This mixture was refluxed at 110° C. for 10 hours to be reacted. After the reaction was completed, a precipitate in the reaction mixture was collected by suction filtration. The obtained solid was dissolved in toluene and subjected to suction filtration through Florisil, celite, and then alumina. The filtrate was condensed. The obtained solid was recrystallized by a mixed solvent of chloroform and hexane; then 4.1 g of objective 9-(4-bromophenyl)-10-phenylanthracene was obtained as a light yellow powdered solid in a yield of 72%. A synthetic scheme of 9-(4-bromophenyl)-10-phenylanthracene is illustrated below (synthetic scheme b-4).

(b-4)

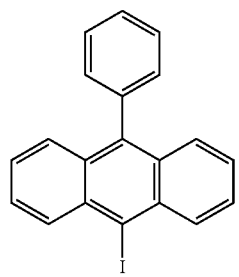 + 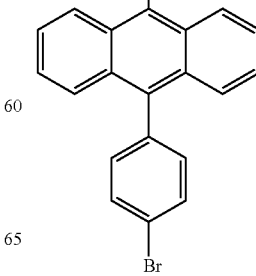 →

Pd(PPh₃)₄
2M Na₂CO₃ aq.
Toluene
reflux

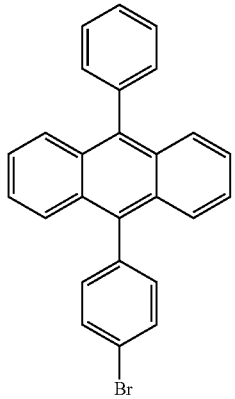

(v) Synthesis method of
4-(10-phenyl-9-anthryl)phenylboronic acid 20.0 g (48.9 mmol) of 9-(4-bromophenyl)-10-phenylanthracene was put into a 500 mL three-necked flask. Then, the atmosphere in the flask was substituted with nitrogen. After 300 mL of tetrahydrofuran (abbreviation: THF) was added to this flask, the flask was put into a constant low temperature bath and the reaction solution was cooled to −78° C. 34.2 mL (53.8 mmol) of n-butyllithium (1.57 mol/L hexane solution) was dropped into this solution and the solution was stirred at −78° C. for 2 hours. Thereafter, 12.6 mL (112 mmol) of trimethyl borate was added to the solution. Then, the flask was taken out from the constant low temperature bath, and the reaction solution was stirred for 24 hours to be returned to room temperature. After the reaction was completed, 200 mL of 1.0 mol/L hydrochloric acid was added to the reaction solution and the reaction solution was stirred at room temperature for 1 hour. An organic layer of the mixture was washed with water and the aqueous layer was extracted with ethyl acetate. The extracted solution was mixed with the organic layer, and the mixture was washed with a saturated aqueous sodium chloride solution, and then dried over magnesium sulfate. After the drying, this mixture was subjected to suction filtration, and the filtrate was condensed to obtain a residue. The obtained residue was recrystallized by a mixed solvent of chloroform and hexane; 15.3 g of objective 4-(10-phenyl-9-anthryl)phenylboronic acid was obtained as a white powdered solid in a yield of 84%. A synthetic scheme of 4-(10-phenyl-9-anthryl)phenylboronic acid is illustrated below (synthetic scheme b-5).

(b-5)

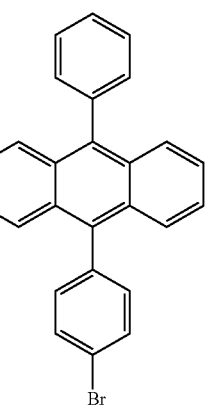

1) n-BuLi, THF, -78° C.
2) B(OMe)₃, -78° C. → R.T.
3) 1M HCl

-continued

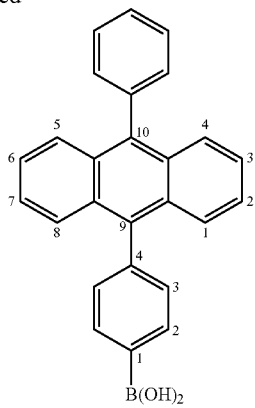

Step 3: Synthesis of (E)-4,4'-bis[4-(10-phenyl-9-anthryl)phenyl]stilbene 2.0 g (5.9 mmol) of (E)-4,4'-dibromostilbene, 4.9 g (13 mmol) of 4-(10-phenyl-9-anthryl)phenylboronic acid, 0.053 g (0.24 mmol) of palladium (II) acetate, and 0.25 g (0.83 mmol) of tri(ortho-tolyl)phosphine were put into a 100 mL three-necked flask. Then, the atmosphere in the flask was substituted with nitrogen. 30 mL of ethylene glycol dimethyl ether (abbreviation: DME) and 18 mL (35 mmol) of an aqueous potassium carbonate solution (2.0 mol/L) were added to the mixture and the mixture was refluxed at 90° C. for 6 hours to be reacted. After the reaction was completed, a precipitate in the reaction mixture was collected by suction filtration. The collected precipitate was washed with toluene; then 4.7 g of objective (E)-4,4'-bis[4-(10-phenyl-9-anthryl)phenyl]stilbene (abbreviation: PAP2S) was obtained as a light yellow powdered solid in a yield of 94%. A synthetic scheme of (E)-4,4'-bis[4-(10-phenyl-9-anthryl)phenyl]stilbene is illustrated below (synthetic scheme c-1).

Figure 8A:
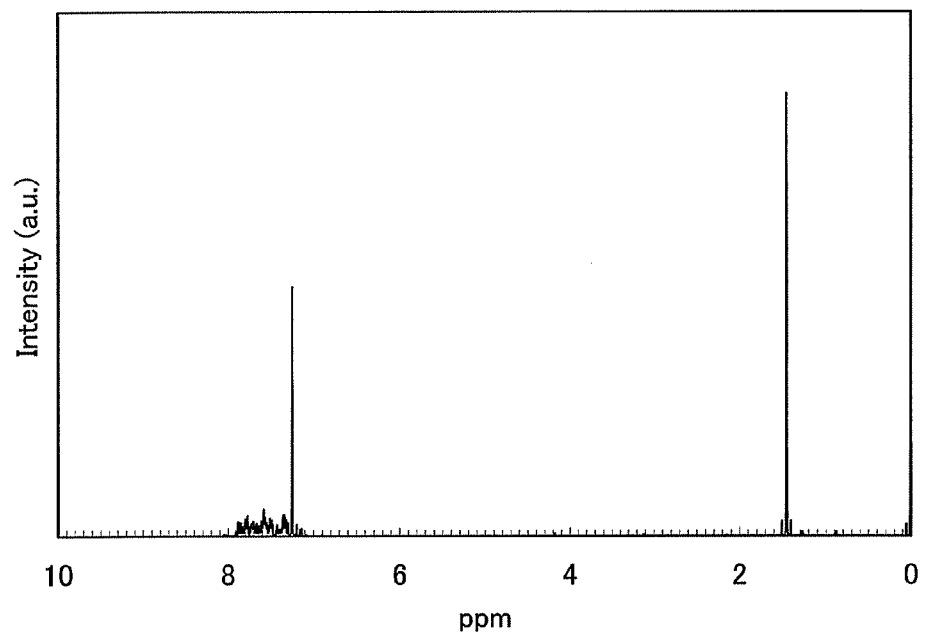
FIGS. 8A and 8B illustrate $^1$H NMR charts of PAP2S.
Figure 8B:
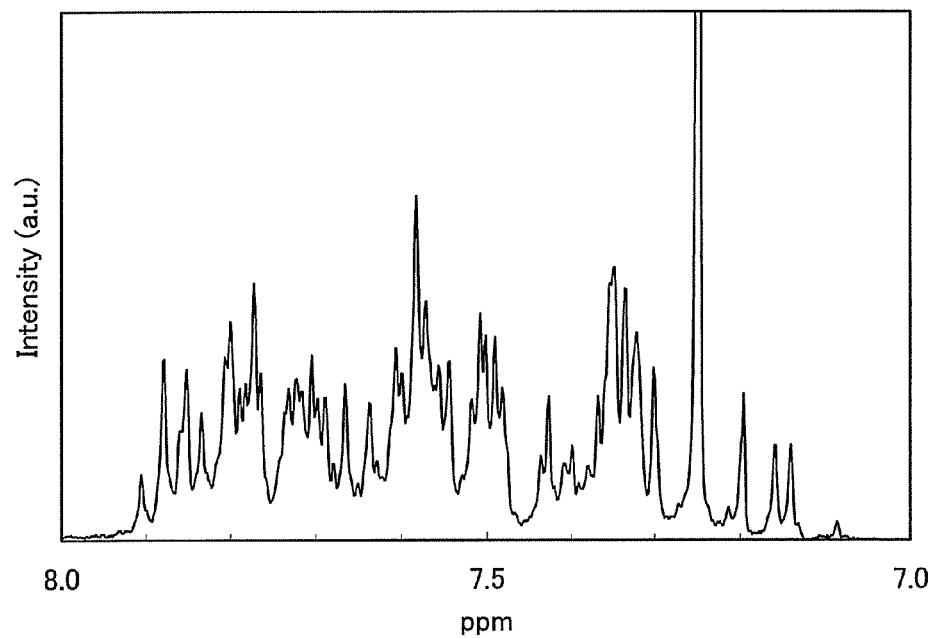

The $^1$H NMR chart is illustrated in each of FIGS. 8A and 8B. It is to be noted that the range of 7.0 to 8.0 ppm in FIG. 8A is expanded and illustrated in FIG. 8B.

Figure 9:
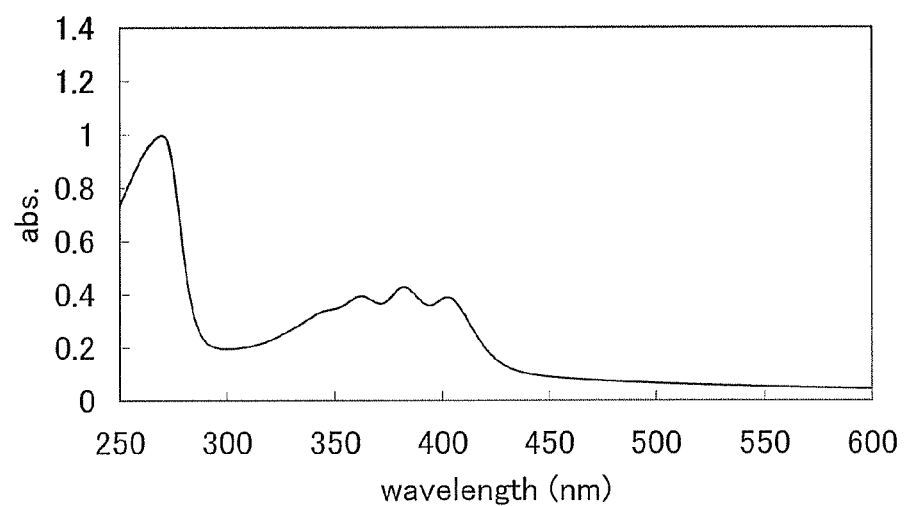
FIG. 9 illustrates an absorption spectrum of PAP2S.
Figure 10:
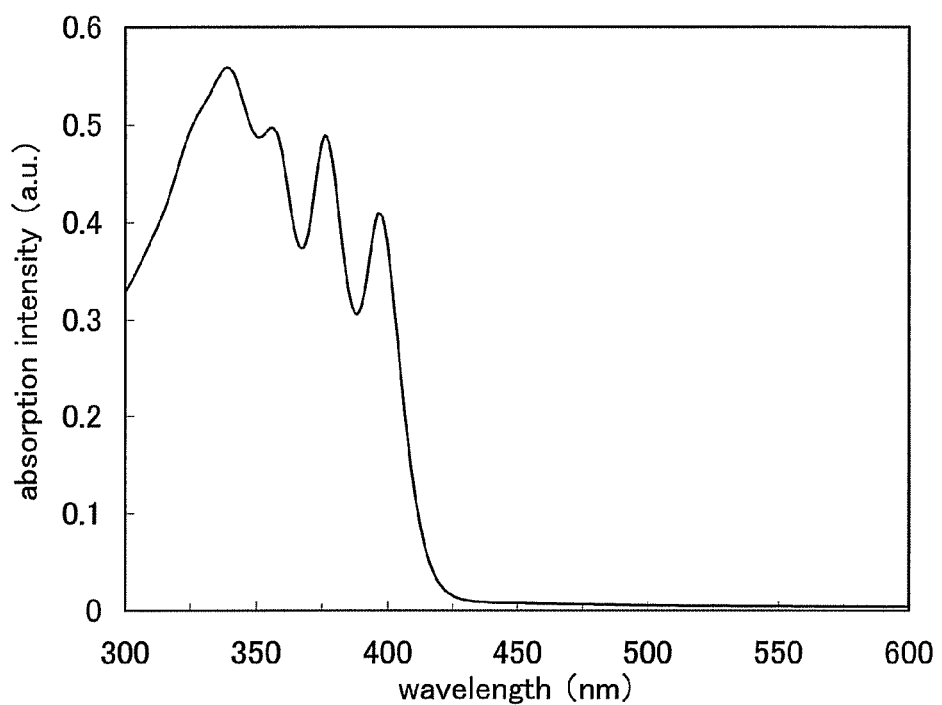
FIG. 10 illustrates an absorption spectrum of PAP2S.
Figure 11:
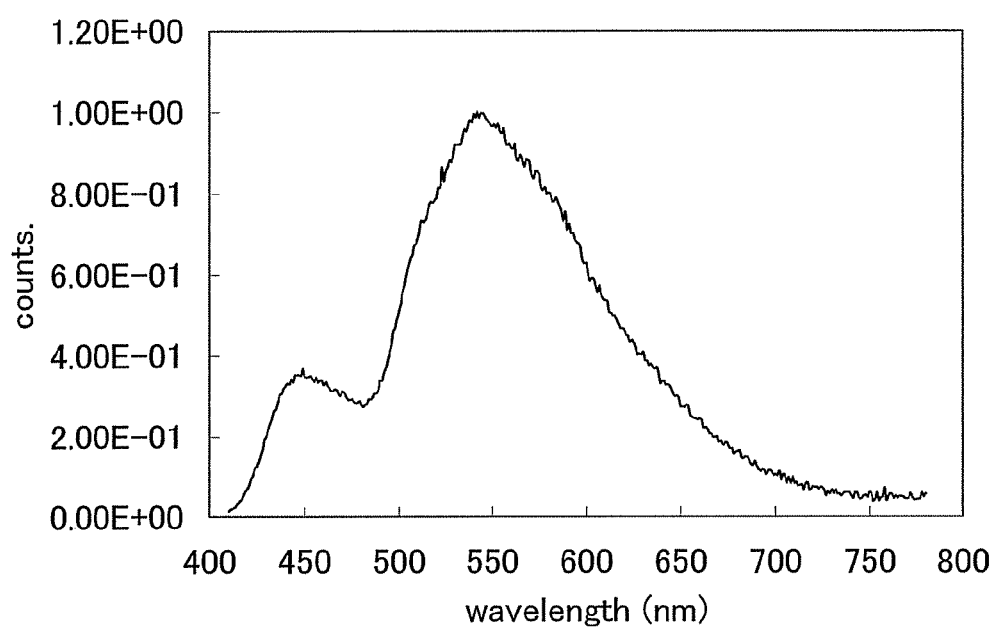
FIG. 11 illustrates an emission spectrum of PAP2S.
Figure 12:
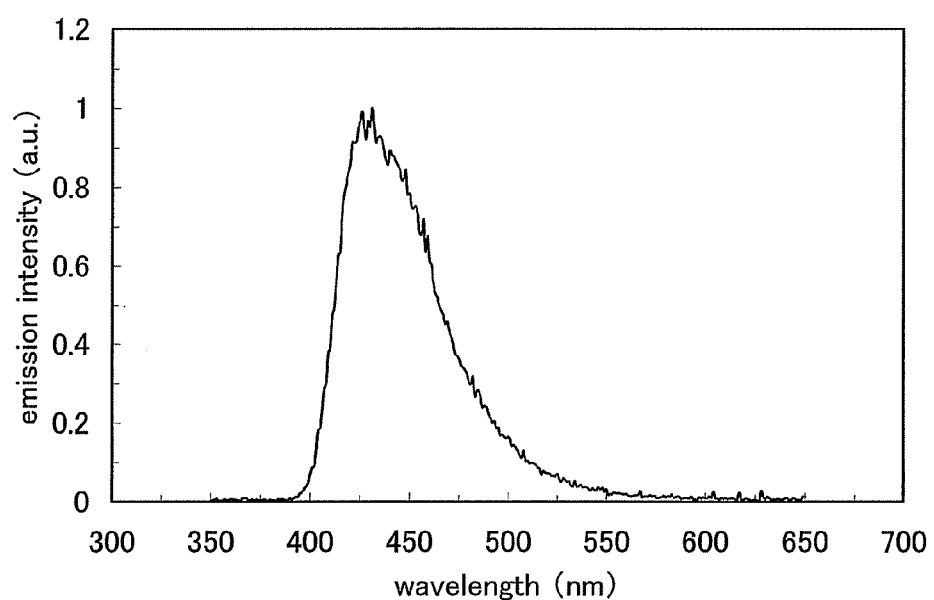
FIG. 12 illustrates an emission spectrum of PAP2S.

The obtained PAP2S was formed into a film by evaporation. Then, an absorption spectrum of PAP2S in a thin film state was measured using a UV/visible spectrophotometer (V-550, manufactured by JASCO Corporation). In each of FIGS. 9 and 10, the absorption spectrum of PAP2S is illustrated, and a horizontal axis and a longitudinal axis indicate a wavelength (nm) and intensity (arbitrary unit), respectively. The absorption spectrum in a thin film state is illustrated in FIG. 9. The absorption spectrum in the state where PAP2S was dissolved in a toluene solution is illustrated in FIG. 10. Further, in each of FIGS. 11 and 12, an emission spectrum of PAP2S is illustrated, and a horizontal axis and a longitudinal axis indicate a wavelength (nm) and emission intensity (arbitrary unit), respectively. The emission spectrum in a thin film state (excitation wavelength 402 nm) is illustrated in FIG. 11. The emission spectrum in the state where PAP2S was dissolved in a toluene solution (excitation wavelength 341 nm) is illustrated in FIG. 12. FIG. 11 illustrates that light emitted from PAP2S in a thin film state has peaks in 449 nm and 542 nm. FIG. 12 illustrates that light emitted from PAP2S has a peak in 431 nm in the toluene solution. Further, such light emission was viewed as blue light emission. Therefore, it is found that PAP2S is a substance suitable as a light-emitting substance which provides blue light emission.

Ionization potential of PAP2S in a thin film state measured using a photoelectron spectrometer (AC-2, manufactured by Riken Keiki Co., Ltd.) was 5.72 eV; hence it is found that the HOMO level was −5.72 eV. Further, a wavelength of an absorption edge on a long-wavelength side of an absorption spectrum was estimated through an absorption spectrum of PAP2S in a thin film state by a Tauc plotting assuming a direct transition. As the result, the energy gap was 2.93 eV. The LUMO level obtained from this energy gap and the HOMO level was −2.79 eV.

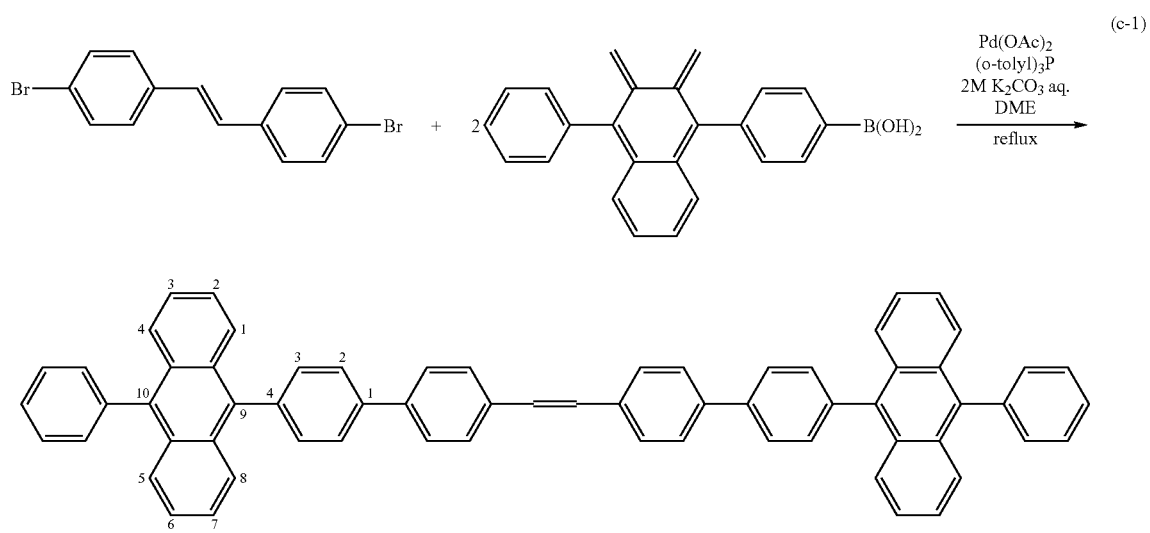

A $^1$H NMR data of the obtained (E)-4,4'-bis[4-(10-phenyl-9-anthryl)phenyl]stilbene is described below. $^1$H NMR (CDCl$_3$, 300 MHz): δ=7.14-7.21 (m, 2H), 7.30-7.44 (m, 11H), 7.48-7.52 (m, 5H), 7.54-7.61 (m, 8H), 7.63-7.73 (m, 8H), 7.77-7.81 (m, 6H), 7.83-7.91 (m, 4H).

A thermogravimetry-differential thermal analysis (TG-DTA) of PAP2S was conducted using a high vacuum differential type differential thermal balance (DTA2410SA, manufactured by Bruker AXS K.K.). The temperature at which the weight is less than or equal to 95% of the weight at the start of the measurement was 475° C. from the relationship between the weight and temperature (thermogravimetry). Accordingly, it is found that PAP2S has an excellent heat resistance.

1.3 g of the obtained (E)-4,4'-bis[4-(10-phenyl-9-anthryl)phenyl]stilbene (abbreviation: PAP2S) was purified by sublimation at 380° C. under a pressure of 5.1 Pa in the flow of argon gas at a rate of 3.0 mL/min; then 0.9 g of PAP2S was collected with a collection rate of 75%.

Figure 13:
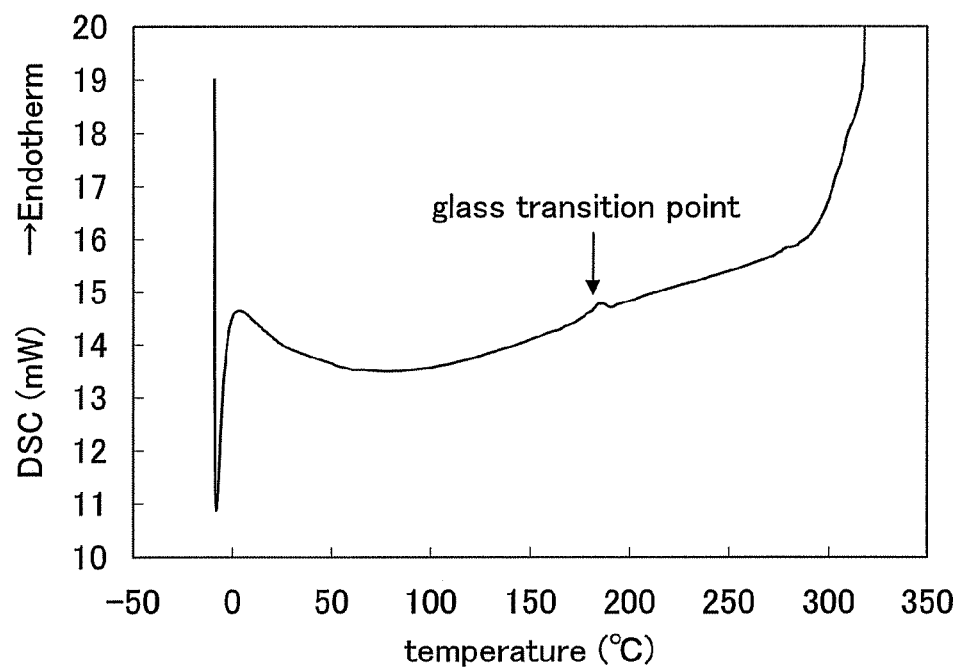
FIG. 13 illustrates a DSC chart of PAP2S.

In addition, a thermophysical property of PAP2S was measured using a differential scanning calorimeter (DSC, manufactured by PerkinElmer, Inc., Pyris 1). First, 4.5 mg of PAP2S was weighed and introduced into the differential scanning calorimeter. Then, PAP2S was heated from −10° C. to 320° C. at a temperature rising rate of 40° C./min. As the result, the DSC chart illustrated in FIG. 13 was obtained. It is found that the glass transition point (Tg) of the PAP2S was 176° C. from this chart. Thus, it is found that PAP2S has a high glass transition point.

This application is based on Japanese Patent Application serial no. 2006-271698 filed in Japan Patent Office on Oct. 3, 2006, the entire contents of which are hereby incorporated by reference.

What is claimed is:

1. An organic material represented by the following general formula (1),

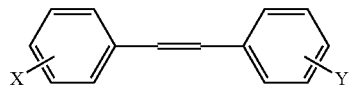

(1)

wherein X and Y in the formula are each a substituent represented by the following general formula (2) or (3) and the same or different from one another

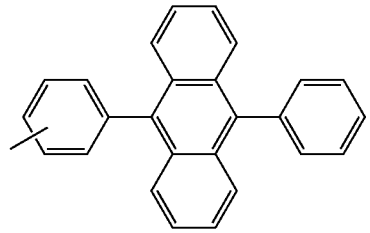

(2)

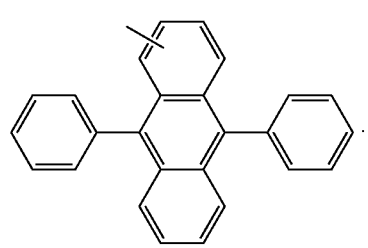

(3)

2. An organic material represented by the following general formula (1),

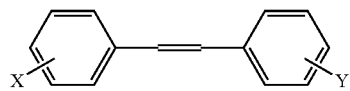

(1)

wherein X and Y in the formula are each a substituent represented by the following general formula (2)

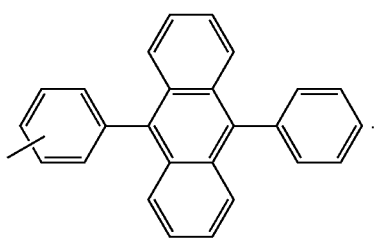

(2)

3. An organic material represented by the following general formula (1),

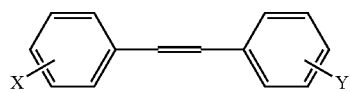

(1)

wherein X and Y in the formula are each a substituent represented by the following general formula (3)

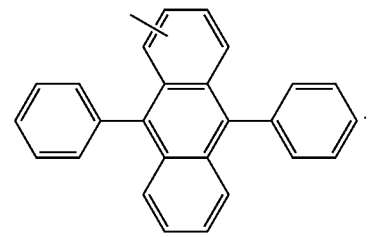

(3)

4. An organic material represented by the following general formula (1),

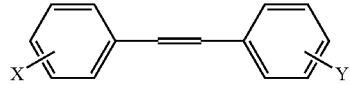

(1)

wherein X in the formula is a substituent represented by the following general formula (2), and Y in the formula is a substituent represented by the following general formula (3)

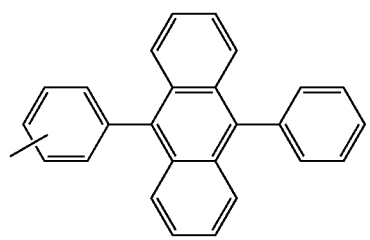
(2)
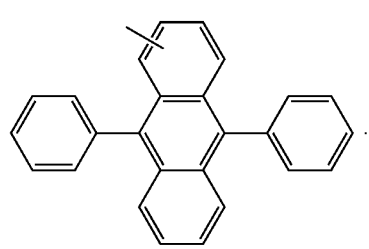
(3)
5. An organic material represented by the following structural formula (4)
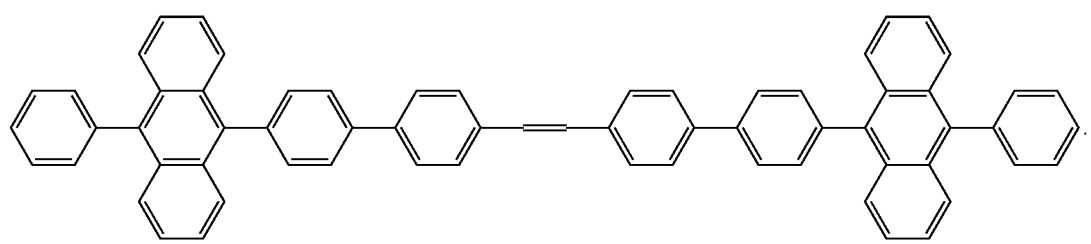
(4)
* * * * *